United States Patent [19]

Polniaszek et al.

[11] Patent Number: 5,856,507

[45] Date of Patent: Jan. 5, 1999

[54] METHODS FOR THE PREPARATION OF BIPHENYL ISOXAZOLE SULFONAMIDES

[75] Inventors: Richard P. Polniaszek, Dayton; Xuebao Wang, East Brunswick; Jeffrey S. DePue, Somerville; Chennagiri R. Pandit, Somerset; Kumar G. Gadamasetti, Princeton Junction; Yadagiri Pendri, Matawan; Eduardo J. Martinez, Plainsboro, all of N.J.

[73] Assignee: Bristol-Myers Squibb Co., Princeton, N.J.

[21] Appl. No.: 786,523

[22] Filed: Jan. 21, 1997

Related U.S. Application Data

[60] Provisional application No. 60/011,974, Feb. 20, 1996.

[51] Int. Cl.$^6$ .................................................. C07D 413/12
[52] U.S. Cl. .......................... 548/241; 548/244; 548/245; 548/246
[58] Field of Search ...................................... 548/241, 244, 548/245, 246

[56] References Cited

U.S. PATENT DOCUMENTS

| | | | |
|---|---|---|---|
| 2,888,455 | 5/1959 | Kano et al. | 540/521 |
| 4,415,496 | 11/1983 | Harris et al. | 540/521 |
| 4,661,479 | 4/1987 | Wyvratt, Jr. et al. | 514/214 |
| 5,236,928 | 8/1993 | Chakravarty et al. | 514/275 |
| 5,270,313 | 12/1993 | Burri et al. | 514/252 |
| 5,292,740 | 3/1994 | Burri et al. | 514/256 |
| 5,378,715 | 1/1995 | Stein et al. | 514/329 |
| 5,464,853 | 11/1995 | Chan et al. | 514/378 |
| 5,514,691 | 5/1996 | Chan et al. | 514/312 |
| 5,514,696 | 5/1996 | Murugesan et al. | 514/380 |
| 5,571,821 | 11/1996 | Chan et al. | 514/312 |
| 5,580,894 | 12/1996 | Scott et al. | 514/380 |
| 5,591,761 | 1/1997 | Chan et al. | 514/380 |
| 5,594,021 | 1/1997 | Chan et al. | 514/378 |
| 5,612,359 | 3/1997 | Murugesan | 514/365 |

FOREIGN PATENT DOCUMENTS

| | | |
|---|---|---|
| 34011/93 | 9/1993 | Australia . |
| 67357/94 | 1/1995 | Australia . |
| 48039/96 | 9/1996 | Australia . |
| 76072 | 4/1983 | European Pat. Off. . |
| 194548 | 9/1986 | European Pat. Off. . |
| 404525 | 12/1990 | European Pat. Off. . |
| 443983 | 8/1991 | European Pat. Off. . |
| 510526 | 10/1992 | European Pat. Off. . |
| 526708 | 2/1993 | European Pat. Off. . |
| 558258 | 9/1993 | European Pat. Off. . |
| 569193 | 11/1993 | European Pat. Off. . |
| 601386 | 6/1994 | European Pat. Off. . |
| 617001 | 9/1994 | European Pat. Off. . |
| 626174 | 11/1994 | European Pat. Off. . |
| 633259 | 1/1995 | European Pat. Off. . |
| 634175 | 1/1995 | European Pat. Off. . |
| 640596 | 3/1995 | European Pat. Off. . |
| 682016 | 11/1995 | European Pat. Off. . |
| 702012 | 3/1996 | European Pat. Off. . |
| 725067 | 8/1996 | European Pat. Off. . |
| 749964 | 12/1996 | European Pat. Off. . |
| 1059459 | 6/1959 | Germany . |
| 0364506 | 11/1962 | Switzerland . |
| 804036 | 11/1958 | United Kingdom . |
| 0897440 | 5/1962 | United Kingdom . |
| 1473433 | 5/1977 | United Kingdom . |
| 2228933 | 9/1990 | United Kingdom . |
| 91/15479 | 10/1991 | WIPO . |
| 93/08799 | 5/1993 | WIPO . |
| 93/10094 | 5/1993 | WIPO . |
| 93/23404 | 11/1993 | WIPO . |
| 94/27979 | 12/1994 | WIPO . |
| 95/26957 | 10/1995 | WIPO . |
| 96/31492 | 10/1996 | WIPO . |
| 96/40681 | 12/1996 | WIPO . |

OTHER PUBLICATIONS

S. Norio et al., Chemical Abstracts, vol. 70, No. 19, (1969), 87639g.
T. Saito, Chemical Abstracts, vol. 73, No. 23 (1970), 120511w.
Derwent Abstract No. 88–289069/41 Feb. 27, 1987.
Derwent Abstract No. 88–195835/28 Nov. 26, 1986.
Derwent Abstract No. 88–061295/09 Jul. 9, 1986.
Derwent Abstract No. 87–152485/22 Oct. 11, 1985.
Derwent Abstract No. 62299 E/30 Dec. 11, 1980.
Derwent Abstract No. 40927 D/23 Sep. 11, 1979.
Derwent Abstract No. 91–254550/35 Feb. 19, 1990.
Derwent Abstract No. 86–246709/38 Nov. 27, 1985.
Derwent Abstract No. 35012 K/15 Sep. 24, 1981.
Allen et al., "Preparation . . . antagonists", CA116(11):106284Z, p. 778, 1992.
R.D. Desai et al., Chemical Abstracts, vol. 71, No. 11, (1969) 49825c.
R.D. Desai et al., Chemical Abstracts, vol. 71, No. 3, (1969) 12872q.
P. G. Ferrini et al., Angew. Chem. Internat. Edit., vol. 2, No. 2 (1963) p. 99.
A. M. van Leusen, et al., "Synthesis . . . Compounds", J. Org. Chem., vol. 41, No. 4, (1976), pp. 69–71.
W. J. Hammar et al., J. Heterocyclic Chem., vol. 18, (1981) pp. 885–888.
A. M. van Leusen et al., Tetrahedron Letters, No. 23, (1972), pp. 2369–2372.
Chan et al., "Identification of a New Class of $ET_A$ Selective Endothelin Antagonists by Pharmacophore Directed Screening", Biochemical and Biophysical Research Communications, vol. 201, No. 1, May 30, 1994, pp. 228–234.

(List continued on next page.)

*Primary Examiner*—Johann Richter
*Assistant Examiner*—Laura R. C. Lutz
*Attorney, Agent, or Firm*—Suzanne E. Babajko

[57] ABSTRACT

Methods for the preparation of biphenyl isoxazole sulfonamides and intermediates thereof. The present invention also relates to the novel intermediates prepared by these methods. The biphenyl isoxazole sulfonamides prepared by the present methods are endothelin antagonists useful, inter alia, for the treatment of hypertension.

10 Claims, No Drawings

OTHER PUBLICATIONS

Stein et al., "The Discovery of Sulfonamide Endothelin Antagonists and the Development of the Orally Active $ET_A$ Antagonists 5–(Dimethylamino)–N–(3, 4–dimethyl–5–isoxazolyl)–1–naphthalenesulfonamide", J. Med. Chem., vol. 37, No. 3, Feb. 4, 1994, pp. 329–331.

Doherty, J. Med. Chem., 35(9), 1493–1508 (May 1992).

CA 65: 2241d (1966).

CA 92:41908v (1979).

Wang et al., "Nitrile . . . sinomin," CA 108:94444w, p. 651 (1988).

Khanna, "Oral . . . formulation," CA 115:35728p, p. 415 (1991).

Stein et al., "The Discovery . . . 1–naphthalenesulfonamide," CA 120:18233n, pp. 21–22 (1994).

Vree et al., "Renal excretion . . . function," CA 97:84685r, p. 23 (1982).

Oie, "Pharmacokinetics . . . dosing," CA102:197512x, p. 18 (1985).

Murugesan et al., "N–(heteroaryl) . . . antagonists," CA 120:270370c, p. 1067 (1994).

Williams, "A General, One–Pot Method for the Synthesis of 2–Substituted Oxazoles", Tetrahedron Letters, vol. 33, No. 8, pp. 1033–1036 (1992).

Cass, "2–Phenyloxazole and ortho–Substituted Derivatives", J. Am. Chem. Soc., vol. 64, pp. 785–787 (1942).

Smith et al., "Mechanistic Studies of the Suzuki Cross–Coupling Reaction", J. Org. Chem., vol. 59, pp. 8151–8156 (1994).

Hunt et al., Tet. Lett., 34(22), 3599–3602, 1993.

Suginome et al., J. Chem. Soc., Chem. Commun., (24), 2777–78, 1996.

Nilsson et al., Acta Chem. Scand., Ser. B, B41(8), 569–76, 1987.

Desurmont et al., J. Org. Chem., 61(22), 7943–46, 1996.

Deloux et al., Jo. Org. Chem., 60(11), 3276–77, 1995.

METHODS FOR THE PREPARATION OF BIPHENYL ISOXAZOLE SULFONAMIDES

This application claims priority from provisional U.S. application Ser. No. 60/011,974, filed Feb. 20, 1996, incorporated herein by reference in its entirety.

FIELD OF THE INVENTION

The present invention relates to methods for the preparation of biphenyl isoxazole sulfonamides and intermediates thereof. The present invention also relates to the novel intermediates prepared by these methods. The biphenyl isoxazole sulfonamides prepared by the present methods are endothelin antagonists useful, inter alia, for the treatment of hypertension.

BRIEF DESCRIPTION OF THE INVENTION

The present methods allow preparation of biphenyl sulfonamides of the following formula I:

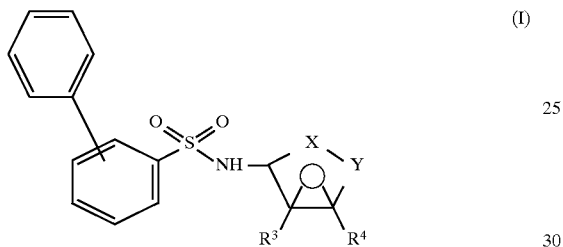

(I)

where the phenyl rings of the biphenyl group may independently be unsubstituted or substituted with one or more substituent groups, enantiomers and diastereomers, and salts, preferably pharmaceutically acceptable salts, thereof. Preferred substituent groups for the biphenyl group include those groups $R^{11}$ to $R^{14}$ described herein and especially, when the biphenyl group is a 2-biphenyl group, the group

in the 4'-position. Preferred methods of the present invention allow preparation of compounds of the following formula Ia:

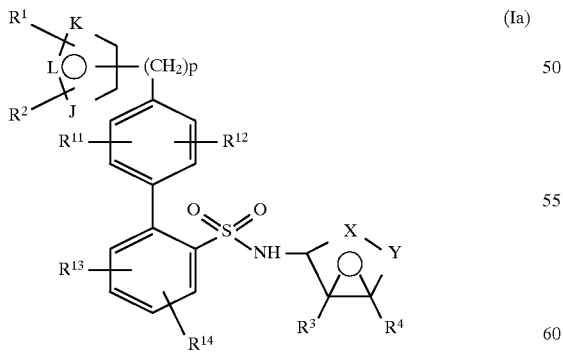

(Ia)

enantiomers and diastereomers, and salts, preferably pharmaceutically acceptable salts, thereof. Throughout this specification, the above symbols are defined as follows:

one of X and Y is N and the other is O;

$R^1$, $R^2$, $R^3$ and $R^4$ are each directly bonded to a ring carbon and are each independently (a) hydrogen;
(b) alkyl, alkenyl, alkynyl, alkoxy, cycloalkyl, cycloalkylalkyl, cycloalkenyl, cycloalkenylalkyl, aryl, aryloxy, aralkyl or aralkoxy, any of which may be substituted with $Z^1$, $Z^2$ and $Z^3$;
(c) halo;
(d) hydroxyl;
(e) cyano;
(f) nitro;
(g) —C(O)H or —C(O)$R^5$;
(h) —CO$_2$H or —CO$_2R^5$;
(i) —$Z^4$—NR$^6$R$^7$;
(j) —$Z^4$—N(R$^{10}$)—$Z^5$—NR$^8$R$^9$; or
(k) $R^3$ and $R^4$ together may also be alkylene or alkenylene, either of which may be substituted with $Z^1$, $Z^2$ and $Z^3$, completing a 4- to 8-membered saturated, unsaturated or aromatic ring together with the carbon atoms to which they are attached;

$R^5$ is alkyl, alkenyl, alkynyl, cycloalkyl, cycloalkylalkyl, cycloalkenyl, cycloalkenylalkyl, aryl or aralkyl, any of which may be substituted with $Z^1$, $Z^2$ and $Z^3$;

$R^6$, $R^7$, $R^8$, $R^9$ and $R^{10}$ are each independently
(a) hydrogen; or
(b) alkyl, cycloalkyl, cycloalkylalkyl, cycloalkenylalkyl, aryl or aralkyl, any of which may be substituted with $Z^1$, $Z^2$ and $Z^3$; or $R^6$ and $R^7$ together may be alkylene or alkenylene, either of which may be substituted with $Z^1$, $Z^2$ and $Z^3$, completing a 3- to 8-membered saturated or unsaturated ring together with the nitrogen atom to which they are attached; or any two of $R^8$, $R^9$ and $R^{10}$ together are alkylene or alkenylene, either of which may be substituted with $Z^1$, $Z^2$ and $Z^3$, completing a 3- to 8-membered saturated or unsaturated ring together with the atoms to which they are attached;

$R^{11}$, $R^{12}$, $R^{13}$ and $R^{14}$ are each independently
(a) hydrogen;
(b) alkyl, alkenyl, alkynyl, alkoxy, cycloalkyl, cycloalkylalkyl, cycloalkenyl, cycloalkenylalkyl, aryl, aryloxy, aralkyl or aralkoxy, any of which may be substituted with $Z^1$, $Z^2$ and $Z^3$,
(c) heterocycle, substituted heterocycle or heterocyclooxy;
(d) halo;
(e) hydroxyl;
(f) cyano;
(g) nitro;
(h) —C(O)H or —C(O)$R^5$;
(i) —CO$_2$H or —CO$_2R^5$;
(j) —SH, —S(O)$_n$R$^5$, —S(O)$_m$—OH, —S(O)$_m$—OR$^5$, —O—S(O)m—OR$^5$, —O—S(O)$_m$OH or —O—S(O)$_m$—OR$^5$;
(k) —$Z^4$—NR$^6$R$^7$; or
(l) —$Z^4$—N(R$^{10}$)—$Z^5$—NR$^8$R$^9$;

$Z^1$, $Z^2$ and $Z^3$ are each independently
(a) hydrogen;
(b) halo;
(c) hydroxy;
(d) alkyl;
(e) alkenyl;
(f) aryl;
(g) aralkyl;
(h) alkoxy;
(i) aryloxy;
(j) aralkoxy;
(k) heterocycle, substituted heterocycle or heterocyclooxy;

(1) —SH, —S(O)$_n$Z$^6$, —S(O)$_m$—OH, —S(O)$_m$—OZ$^6$, —O—S(O)$_m$—Z$^6$, —O—S(O)$_m$OH or —O—S(O)$_m$—OZ$^6$;

(m) oxo;
(n) nitro;
(o) cyano;
(p) —C(O)H or —C(O)Z$^6$;
(q) —CO$_2$H or —CO$_2$Z$^6$;
(r) —Z$^4$—NZ$^7$Z$^8$;
(s) —Z$^4$—N(Z$^{11}$)—Z$^5$—H;
(t) —Z$^4$—N(Z$^{11}$)—Z$^5$—Z$^6$; or
(u) —Z$^4$—N(Z$^{11}$)—Z$^5$—NZ$^7$Z$^8$;

Z$^4$ and Z$^5$ are each independently
(a) a single bond;
(b) —Z$^9$—S(O)$_n$—Z$^{10}$—;
(c) —Z$^9$—C(O)—Z$^{10}$—;
(d) —Z$^9$—C(S)—Z$^{10}$—;
(e) —Z$^9$—O—Z$^{10}$—;
(f) —Z$^9$—S—Z$^{10}$—;
(g) —Z$^9$—O—C(O)—Z$^{10}$—; or
(h) —Z$^9$—C(O)—O—Z$^{10}$—;

Z$^6$ is alkyl; alkyl substituted with one to three groups selected from halogen, aryl, aryloxy and alkoxy; alkenyl; alkynyl; cycloalkyl; cycloalkyl substituted with one to three groups selected from alkyl, aryl, alkenyl and alkoxyaryl; cycloalkyl to which is fused a benzene ring; aryloxy substituted with one or two halogens; cycloalkylalkyl; cycloalkenyl; cycloalkenylalkyl; aryl; aryl substituted with methylenedioxy or one to four groups selected from alkyl, dialkylamino, cyano, halogen, trihaloalkyl, alkoxy and trihaloalkoxy; or heterocycle or substituted heterocycle;

Z$^7$ and Z$^8$ are each independently hydrogen, alkyl, cycloalkyl, cycloalkylalkyl, cycloalkenylalkyl, aryl or aralkyl, or Z$^7$ and Z$^8$ together are alkylene or alkenylene, completing a 3- to 8-membered saturated or unsaturated ring together with the nitrogen atom to which they are attached;

Z$^9$ and Z$^{10}$ are each independently a single bond, alkylene, alkenylene or alkynylene;

Z$^{11}$ is
(a) hydrogen; or
(b) alkyl, alkyl substituted with one, two or three halogens, cycloalkyl, cycloalkylalkyl, cycloalkenylalkyl, aryl or aralkyl;

or any two of Z$^7$, Z$^8$ and Z$^{11}$ together are alkylene or alkenylene, completing a 3- to 8-membered saturated or unsaturated ring together with the atoms to which they are attached;

J is O, S, N or NR$^{15}$;
K and L are N or C, provided that at least one of K or L is C;
R$^{15}$ is hydrogen, alkyl, hydroxyethoxy methyl or methoxyethoxy methyl;
each m is independently 1 or 2;
each n is independently 0, 1 or 2; and
p is 0 or an integer from 1 to 2.

In accordance herewith, a compound of the formula I or salt thereof may be prepared by a method comprising the steps of:

(a) contacting a pinacol ester of the formula II or salt thereof:

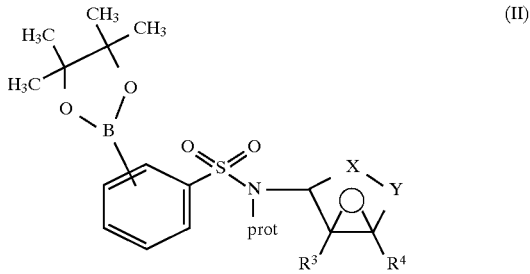

where the phenyl ring of said formula II may be further substituted, such as with one or more groups described for the groups R$^{11}$ to R$^{14}$ herein, with a halophenyl compound of the formula III or salt thereof:

where the phenyl ring of said formula III may be further substituted, such as with one or more groups described for the groups R$^{11}$ to R$^{14}$ herein, and especially, when the biphenyl group of said compound of the formula I or salt thereof is a 2-biphenyl, the group

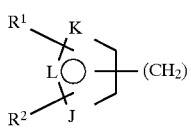

para to the halo group, in the presence of a palladium(0) catalyst and, preferably, a base, to form a nitrogen-protected compound of the formula IV or salt thereof:

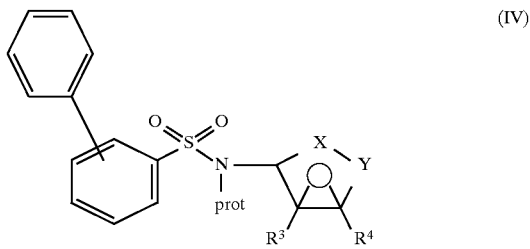

where the phenyl rings of the biphenyl group may independently be unsubstituted or substituted with one or more substituent groups; and (b) deprotecting the nitrogen of said compound of the formula IV or salt thereof to form said compound of the formula I or salt thereof.

"Prot", as used in formula II and throughout this specification, denotes a nitrogen-protecting group, which may be any suitable nitrogen-protecting group such as 2-ethoxyethyl, 2-methoxypropyl, methoxyethoxymethyl or those described in European Patent Application Publication No. 569;193 (1993), incorporated herein by reference, and is preferably methoxyethoxymethyl ("MEM"). The halo group in formula III is preferably bromo or iodo, most preferably iodo.

In a preferred embodiment, a compound of the formula Ia or salt thereof may be prepared by a method comprising the steps of:

(a) contacting a pinacol ester of the formula IIa or salt thereof:

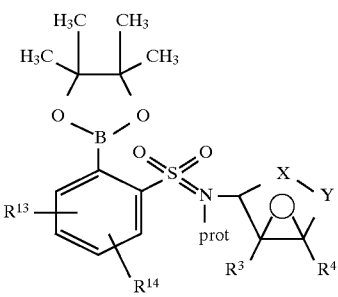

with a halophenyl compound of the formula IIIa or salt thereof:

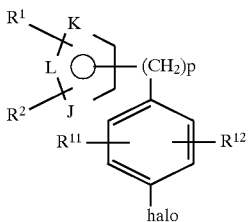

in the presence of a palladium(0) catalyst and, preferably, a base, to form a nitrogen-protected compound of the formula IVa or salt thereof:

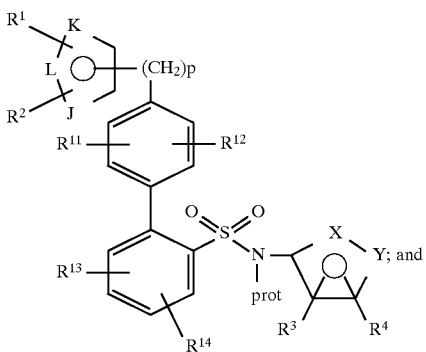

(b) deprotecting the nitrogen of said formula IVa compound or salt thereof to form said compound of the formula Ia or salt thereof.

The present methods for preparing a compound of the formula I or salt thereof are advantageous in that they provide high yields with minimal or no formation of impurities.

Further provided herewith are novel intermediates of the present methods, and novel methods for preparing such intermediates.

DETAILED DESCRIPTION OF THE INVENTION

The present invention is described further as follows. Listed below are definitions of terms used in this specification. These definitions apply to the terms as used throughout this specification, individually or as part of another group, unless otherwise indicated in specific instances.

The term "alkyl" or "alk-" refers to straight or branched chain hydrocarbon groups having 1 to 10 carbon atoms, preferably 1 to 7 carbon atoms. The expression "lower alkyl" refers to alkyl groups of 1 to 4 carbon atoms.

The term "alkoxy" refers to alkyl-O-.

The term "aryl" or "ar-" refers to phenyl, naphthyl and biphenyl.

The term "alkenyl" refers to straight or branched chain hydrocarbon groups of 2 to 10 carbon atoms having at least one double bond. Groups of two to four carbon atoms are preferred.

The term "alkynyl" refers to straight or branched chain groups of 2 to 10 carbon atoms having at least one triple bond. Groups of two to four carbon atoms are preferred.

The term "alkylene" refers to a straight chain bridge of 1 to 5 carbon atoms connected by single bonds (e.g., —($CH_2$)x— wherein x is 1 to 5), which may be substituted with 1 to 3 lower alkyl groups.

The term "alkenylene" refers to a straight chain bridge of 2 to 5 carbon atoms having one or two double bonds that is connected by single bonds and may be substituted with 1 to 3 lower alkyl groups. Exemplary alkenylene groups are —CH=CH—CH=CH—, —$CH_2$—CH=CH—, —$CH_2$—CH=CH—$CH_2$—, —C($CH_3$)$_2$CH=CH— and —CH($C_2H_5$)—CH=CH—.

The term "alkynylene" refers to a straight chain bridge of 2 to 5 carbon atoms that has a triple bond therein, is connected by single bonds, and may be substituted with 1 to 3 lower alkyl groups. Exemplary alkynylene groups are —C≡C—, —$CH_2$—C≡C—, —CH($CH_3$)—C≡C— and —C≡C—CH($C_2H_5$)$CH_2$—.

The term "alkanoyl" refers to groups of the formula —C(O)alkyl.

The terms "cycloalkyl" and "cycloalkenyl" refer to cyclic hydrocarbon groups of 3 to 8 carbon atoms.

The term "hydroxyalkyl" refers to an alkyl group including one or more hydroxy radicals such as —$CH_2CH_2$OH, —$CH_2CH_2$OHCH$_2$OH, —CH($CH_2$OH)$_2$ and the like.

The terms "halogen" and "halo" refer to fluorine, chlorine, bromine and iodine.

The terms "heterocycle", "heterocyclic" and "heterocyclo" refer to an optionally substituted, fully saturated or unsaturated, aromatic or nonaromatic cyclic group, for example, which is a 4 to 7 membered monocyclic, 7 to 11 membered bicyclic, or 10 to 15 membered tricyclic ring system, which has at least one heteroatom in at least one carbon atom-containing ring. Each ring of the heterocyclic group containing a heteroatom may have 1, 2 or 3 heteroatoms selected from nitrogen atoms, oxygen atoms or sulfur atoms, where the nitrogen and sulfur heteroatoms may optionally be oxidized and the nitrogen heteroatoms may optionally be quaternized. The heterocyclic group may be attached at any heteroatom or carbon atom.

Exemplary monocyclic heterocyclic groups include pyrrolidinyl, pyrrolyl, pyrazolyl, oxetanyl, pyrazolinyl imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, and the like.

Exemplary bicyclic heterocyclic groups include indolyl, benzothiazolyl, benzoxazolyl, benzothienyl, quinuclidinyl, quinolinyl, tetra-hydroisoquinolinyl, isoquinolinyl, benzimidazolyl, benzopyranyl, indolizinyl, benzofuryl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]pyridinyl] or furo[2,3-b]

pyridinyl), dihydroisoindolyl, dihydroquinazolinyl (such as 3,4-dihydro-4-oxo-quinazolinyl), tetrahydroquinolinyl and the like.

Exemplary tricyclic heterocyclic groups include carbazolyl, benzidolyl, phenanthrolinyl, acridinyl, phenanthridinyl, xanthenyl and the like.

The expression "substituted heterocycle" refers to a heterocycle substituted with 1, 2 or 3 of the following:

(a) alkyl, especially lower alkyl;
(b) hydroxy (or protected hydroxy);
(c) halo;
(d) oxo (i.e.=O);
(e) amino, alkylamino or dialkylamino;
(f) alkoxy;
(g) carbocyclo, such as cycloalkyl;
(h) carboxy;
(i) heterocyclooxy;
(j) alkoxycarbonyl, such as unsubstituted lower alkoxycarbonyl;
(k) carbamyl, alkylcarbamyl or dialkylcarbamyl;
(l) mercapto;
(m) nitro;
(n) cyano;
(o) carboalkoxy;
(p) sulfonamido, sulfonamidoalkyl or sulfonamidodialkyl;

(q) 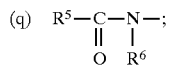

(r) 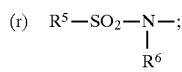

(s) aryl;
(t) alkylcarbonyloxy;
(u) arylcarbonyloxy;
(v) arylthio;
(w) aryloxy;
(x) alkylthio;
(y) formyl;
(z) arylalkyl; or
(a') aryl substituted with alkyl, cycloalkyl, alkoxy, hydroxy, amino, alkylamino, dialkylamino, halo or trihaloalkyl.

The term "heterocyclooxy" denotes a heterocyclic group bonded through an oxygen bridge.

Throughout the specification, groups and substituents thereof may be chosen to provide stable moieties and compounds.

The compounds of formula I and intermediates thereof may form salts which are also within the scope of this invention. Pharmaceutically acceptable (i.e., non-toxic, physiologically acceptable) salts are preferred, although other salts are also useful, for example, in isolating or purifying the compounds of this invention.

The compounds of formula I and intermediates thereof may form salts with alkali metals such as sodium, potassium and lithium, with alkaline earth metals such as calcium and magnesium, with organic bases such as dicyclohexylamine, t-butyl amine, benzathine, N-methyl-D-glucamide and hydrabamine, and with amino acids such as arginine, lysine and the like. Such salts may be obtained by reacting these compounds with the desired ion in a medium in which the salt precipitates or in an aqueous medium followed by lyophilization.

When groups such as the $R^1$ to $R^4$ or $R^{11}$ to $R^{14}$ substituents comprise a basic moiety, such as amino or substituted amino, the compounds of formula I and intermediates thereof may form salts with a variety of organic and inorganic acids. Such salts include those formed with hydrochloric acid, hydrogen bromide, methanesulfonic acid, sulfuric acid, acetic acid, maleic acid, benzenesulfonate, toluenesulfonate and various other sulfonates, nitrates, phosphates, borates, acetates, tartrates, maleates, citrates, succinates, benzoates, ascorbates, salicylates and the like. Such salts may be formed by reacting these compounds in an equivalent amount of the acid in a medium in which the salt precipitates or in an aqueous medium followed by lyophilization.

In addition, when groups such as the $R^1$ to $R^4$ or $R^{11}$ to $R^{14}$ substituents comprise a basic moiety such as amino, zwitterions ("inner salts") may be formed.

Certain groups such as the $R^1$ to $R^4$ and $R^{11}$ to $R^{14}$ substituents of the compounds of the invention may contain asymmetric carbon atoms. The compounds of the invention such as those of the formula I and salts thereof may exist, therefore, in enantiomeric and diastereomeric forms and in racemic mixtures thereof. All are within the scope of this invention. Additionally, compounds such as those of formula I and salts thereof may exist as enantiomers even in the absence of asymmetric carbons. All such enantiomers are within the scope of this invention.

U.S. patent application Ser. No. 08/493,331, filed Jul. 24, 1995 (Attorney Docket No. HA662c) by Murugesan et al. and continuation-in-part thereof U.S. patent application Ser. No. 08/603,975, filed Feb. 20, 1996 (Attorney Docket No. HA662d) by Murugesan et al., entitled "Substituted Biphenyl Isoxazole Sulfonamides", describing endothelin antagonists, starting materials and methods, are each incorporated herein by reference in its entirety.

Coupling of Formulae II and III Compounds, and Deprotection

A compound of the formula I or salt thereof may be prepared by coupling a pinacol ester of the formula II or salt thereof with a halophenyl compound of the formula III or salt thereof, and by deprotecting the nitrogen-protected compound IV or salt thereof formed by the aforementioned coupling.

Coupling of compounds of the formulae II and III or salts thereof is conducted in the presence of a palladium(0) catalyst, preferably palladium acetate/triphenylphosphine or other palladium (II) salt/triphenylphosphine, tetrakisphenylphosphine palladium or tris(dibenzylideneacetone) dipalladium, and, preferably, a base, preferably aqueous potassium carbonate or sodium carbonate, to form a nitrogen-protected compound of the formula IV or salt thereof. The preferred molar ratio of palladium (II) salt to triphenylphosphine is between 1:1 and 1:3. See the conditions for catalysis described by A. Suzuki et al., *Pure & Applied Chemistry*, 63, 419–422 (1991); A. Martin et al., *Acta. Chem. Scand.*, 47, 221 (1993); H. Jendralla et al., *Liebig Ann.*, 1253 (1995), all incorporated herein by reference.

When the halophenyl compound III is a compound IIIa, protection of the heteroatoms J and K or L may be desirable, in certain instances, to facilitate the coupling reaction. For example, when J and K or L are N, one of the groups may be protected by a suitable protecting group such as t-butoxycarbonyl, etc. Specific $R^{11}$–$R^{14}$ groups may be chosen to be compatible with the reaction conditions. Additionally, specific $R^{11}$–$R^{14}$ groups may be converted into alternative $R^{11}$–$R^{14}$ groups, either before or after coupling, using any suitable methods such as those known in the art.

The coupling method is preferably conducted at a temperature of from about 25° C. to about 100° C. (most preferably from about 45° C. to about 75° C.), at a pressure of about 1 atm, and under an atmosphere of argon or nitrogen. Molar ratios of the pinacol ester II or salt thereof to the halophenyl compound III or salt thereof are preferably from about 1:1 to about 1:1.2. Amounts of palladium(0) catalyst and base are selected to catalyze the coupling reaction and are preferably from about 2.5 mol % to about 10 mol %, and from about 2.5 equivalents to about 7 equivalents, respectively. Solvents are preferably employed which are selected from aqueous or organic liquids such as acetone, ethanol, toluene, tetrahydrofuran, dimethoxyethane and water, or mixtures thereof, preferably a mixture of toluene and ethanol. Amounts of solvent are preferably those wherein the pinacol ester II or salt thereof is from about 4 to about 9% by weight, based on the combined weight of solvent and pinacol ester II or salt thereof. For example, the following are exemplary ranges for solvent/pinacol ester II/base: tetrahydrofuran (30 to 70 mL), toluene (100 to 200 mL), ethanol (80 to 160 mL)/pinacol ester II (15 to 20 g)/aqueous 2M sodium carbonate (100 to 150 mL).

Residual palladium catalyst is preferably removed, either before or after deprotection of the compound of formula IV or salt thereof, by contact with a chelating agent such as trithiocyanuric acid ("TMT"). Crystallization providing a suitable crystalline form of the compound of the formula I or salt thereof, subsequent to deprotection of the compound of the formula IV or salt thereof, is also contemplated by the present invention. Preferably, crystallization is achieved from a supersaturated ethanolic solution, with or without the presence of co-solvents such as heptane or water, especially where seeded with the desired crystalline form. Most preferably, crystallization is conducted by the methods of the Examples herein.

Compounds of the formula III and salts thereof may be prepared by methods analogous to those described in U.S. patent application Ser. No. 08/493,331 and the aforementioned continuation-in-part thereof. Preferably, oxazole compounds of the formula IIIa or salts thereof are prepared by the novel methods for their preparation described herein. Compounds of the formula II and salts thereof are preferably prepared by the novel methods for their preparation described herein.

Deprotection of the formula IV compound or salt thereof formed by the present coupling method may be conducted by any suitable method, such as methods analogous to those described in U.S. patent application Ser. No. 08/493,331 and the aforementioned continuation-in-part thereof. Preferably, when "prot" is MEM, deprotection is conducted by heating in a mixture of aqueous HCl and ethanol.

Preparation of Formula II Compounds

The pinacol esters of the formula II and salts thereof may themselves be formed by novel methods provided herein. In accordance herewith, a pinacol ester of the formula II or salt thereof may be prepared by a method comprising the steps of:

(a) contacting a compound of the formula V or salt thereof:

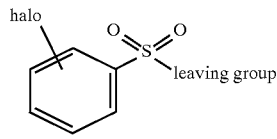

where the phenyl group of said formula V may be further substituted, such as with one or more groups described for the groups $R^{11}$ to $R^{14}$ herein, and where halo is preferably bromo, chloro or iodo, most preferably bromo, with an amine of the formula VI or salt thereof:

in the presence of an organic base and an organic solvent, to form a compound of the formula VII or salt thereof:

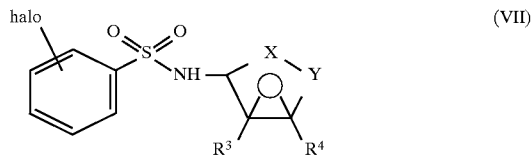

where the phenyl group of said formula VII may be further substituted, such as with one or more groups described for the groups $R^{11}$ to $R^{14}$ herein;

(b) protecting the nitrogen of said compound of the formula VII or salt thereof to form a compound of the formula VIII or salt thereof:

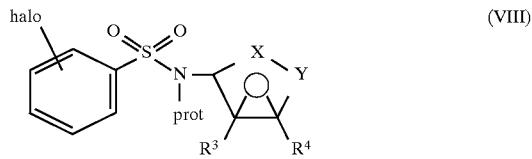

where the phenyl group of said formula VIII may be further substituted, such as with one or more groups described for the groups $R^{11}$ to $R^{14}$ herein;

(c) lithiating said compound of the formula VIII or salt thereof with an alkyl or aryl lithium compound and contacting the lithiated product formed with a trialkylborate, followed by hydrolysis, to form a boronic acid of the formula IX or salt thereof:

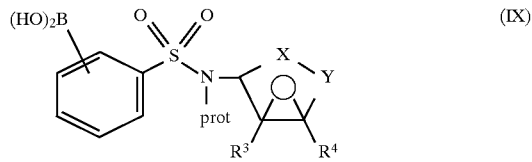

where the phenyl group of said formula IX may be further substituted, such as with one or more groups described for the groups $R^{11}$ to $R^{14}$ herein; and (d) contacting said compound of the formula IX or salt thereof with pinacol (i.e., 2,3-dimethyl-2, 3-butanediol), with removal of water, thereby forming said compound of the formula II or salt thereof.

In a preferred embodiment, a pinacol ester of the formula IIa or salt thereof may be prepared by a method comprising the steps of:

(a) contacting a compound of the formula Va or salt thereof:

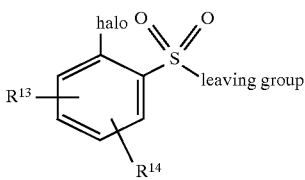

with an amine of the formula VIa or salt thereof:

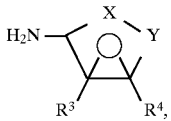

in the presence of an organic base and organic solvent, to form a compound of the formula VIIa or salt thereof:

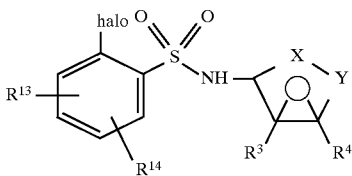

(b) protecting the nitrogen of said compound of the formula VIIa or salt thereof to form a compound of the formula VIIIa or salt thereof:

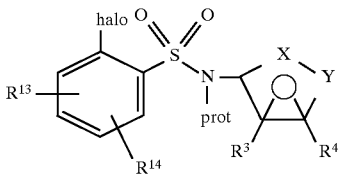

(c) lithiating said compound of the formula VIIIa or salt thereof with an alkyl or aryl lithium compound and contacting the lithiated product formed with a trialkylborate, followed by hydrolysis, to form a boronic acid of the formula IXa or salt thereof:

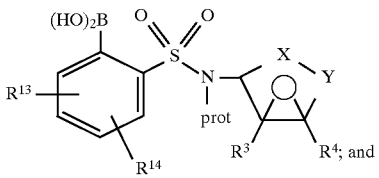

(d) contacting said compound of the formula IXa or salt thereof with pinacol, with removal of water, thereby forming said compound of the formula IIa or salt thereof.

The term "leaving group", as used herein, denotes any suitable leaving group such as a halo group, preferably chloro. Any suitable organic base may be employed in step (a). Preferred organic bases include amines such as pyridine or a trialkylamine. The organic solvent employed in step (a) is preferably a haloalkane, such as dichloromethane or 1,2-dichloroethane, or the organic base, such as neat pyridine, may also function as the solvent.

As described above, compounds of the formula VIII and salts thereof may be prepared by contacting a compound of the formula V or salt thereof with an amine compound of the formula VI or salt thereof, and by protecting the nitrogen of the product compound VII or salt thereof. The formula VIII compound or salt thereof obtained is then lithiated with an alkyl or aryl lithium compound, preferably with n-butyl lithium or phenyl lithium, at temperatures which are preferably from about −40° C. to about −105° C. (especially, from about −70° C. to about −100° C.), to form the compound:

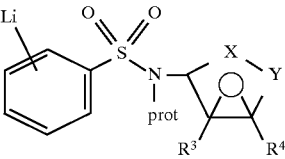

where the phenyl group of said compound may be further substituted, such as with one or more groups described for the groups $R^{11}$ to $R^{14}$ herein, or salt thereof, preferably the compound:

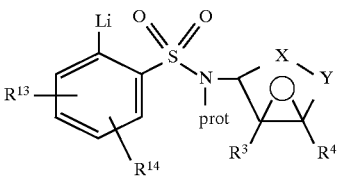

or salt thereof. Treatment of the lithiated compound or salt thereof with a trialkylborate such as triisopropylborate or, preferably, trimethylborate, at temperatures which are preferably from about −40° C. to about −105° C. (especially, from about −70° C. to about −100° C.), provides the following boronate ester:

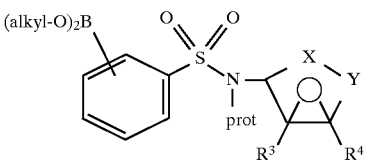

where the phenyl group of said compound may be further substituted, such as with one or more groups described for the groups $R^{11}$ to $R^{14}$ herein, or salt thereof, preferably the boronate ester:

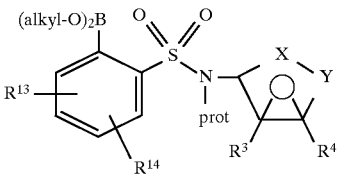

or salt thereof, which may then be hydrolyzed with a suitable acid, preferably an aqueous acid such as aqueous hydrochloric acid, or with a suitable base, to form the boronic acid IX or salt thereof. The hydrolysis step, forming the boronic acid IX or salt thereof, is advantageous as the boronic acid possesses enhanced stability relative to the boronate ester from which it is obtained. The aforementioned steps may be conducted by methods analogous to those described in, and with starting materials of the formulae V and VI and salts thereof prepared by methods analogous to those described in, European Patent Application Publication No. 569,193 (1993) and in U.S. patent application Ser. No. 08/493,331 and the aforementioned continuation-in-part thereof.

The boronic acid IX or salt thereof may then be contacted with pinacol, with the removal of water, to form the corresponding pinacol ester II or salt thereof. Removal of water may be conducted, for example, by the addition of a drying agent such as magnesium sulfate or by azeotropic removal of water by heating with a solvent such as toluene. This reaction is preferably conducted at a temperature of from about 110° C. to about 120° C. (most preferably from about 112° C. to about 115° C.), at a pressure of about 1 atm, and under an atmosphere of argon or nitrogen. Molar ratios of pinacol to the boronic acid IX or salt thereof are preferably from about 1:1 to about 1.1:1. Solvents are preferably employed which are selected from organic liquids such as toluene. Amounts of solvent are preferably those wherein the boronic acid IX or salt thereof is from about 4 to about 10% by weight, based on the combined weight of solvent and boronic acid IX or salt thereof.

The boronic acid IX or salt thereof (preferably, the preferred boronic acid IXa or salt thereof) may be directly coupled with the halophenyl compound III or salt thereof to form a formula IV compound or salt thereof. This method, especially where the halophenyl compound III or salt thereof is an iodophenyl compound III or salt thereof (preferably, an iodophenyl compound IIIa or salt thereof), is also contemplated by the present invention. The pinacol ester II or salt thereof in place of the boronic acid IX or salt thereof may be advantageous, however, as the pinacol ester compounds are highly stable, and lesser amounts of impurities may be formed and higher yields of the formula IV compound or salt thereof may be obtained upon coupling with a halophenyl compound III or salt thereof.

Preparation of Formula III Compounds

Halophenyl compounds of the formula III and salts thereof may be prepared by methods analogous to those described in U.S. patent application Ser. No. 08/493,331 and the aforementioned continuation-in-part thereof. Preferred compounds of the formula IIIa and salts thereof bearing an oxazole ring may also be formed by novel methods provided herein. In accordance herewith, a formula IIIa(1) oxazole or salt thereof may be prepared by a method comprising the steps of:

(a) contacting a phenyl acid halide X or salt thereof:

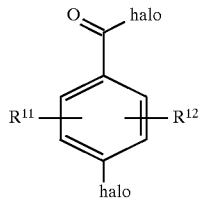  (X)

with an amine acetal XI or salt thereof:

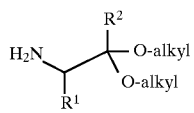  (XI)

in the presence of a base and a solvent, to form an amide acetal of the formula XII or salt thereof:

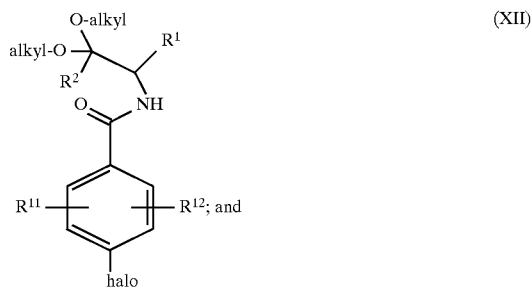  (XII)

(b) cyclizing the amide acetal of the formula XII or salt thereof, in the presence of a cyclization agent, to form an oxazole phenyl halide of the formula IIIa(1) or salt thereof:

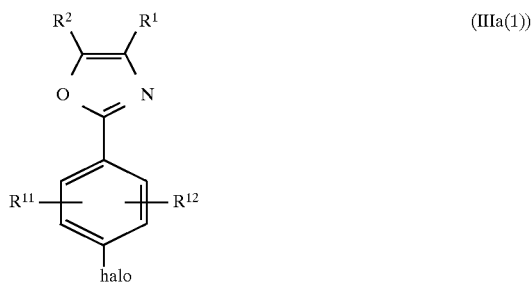  (IIIa(1))

The starting phenyl acid halide X or salt thereof is commercially available or may readily be prepared by one of ordinary skill in the art. The halo group of the acid halide moiety is preferably chloro; the halo group in the position para to the acid halide moiety is preferably bromo, chloro, or iodo, most preferably iodo. The starting amine acetal XI or salt thereof is also commercially available or may readily be prepared by one of ordinary skill in the art. The alkyl groups of the acetal moiety are preferably methyl or ethyl, most preferably, methyl.

The base employed in step (a) may be any suitable base, and is preferably an alkali metal carbonate, bicarbonate or hydroxide, most preferably, potassium bicarbonate (in a solvent such as water and/or acetone) or potassium carbonate (in a solvent such as methylene chloride).

Cyclization is conducted by contacting the amide acetal XII or salt thereof with a cyclization agent which may be any compound effecting the cyclization reaction, and is preferably Eaton's reagent (i.e., methanesulfonic acid and phosphoric oxide) or polyphosphoric acid (PPA), most preferably Eaton's reagent. The cyclization is preferably conducted at a temperature of from about 125° C. to about 150° C. (most preferably from about 130° C. to about 135° C.), at a pressure of about 1 atm, and under an atmosphere of argon or nitrogen. Amounts of cyclization agent are selected to achieve cyclization and are preferably from about (catalyst/substrate) 8 mL/g to about 15 mL/g when Eaton's reagent is employed. Eaton's reagent is a solution of $P_2O_5$ in methanesulfonic acid and can also function as a preferred solvent for the cyclization. Exemplary compositions for Eaton's reagent are those containing 7.5 to 15% by weight $P_2O_5$ in methanesulfonic acid.

The compounds of the formula IIIa and salts thereof may also be used in a further method ("reverse coupling") contemplated by the present invention, for the preparation of compounds of the formula Ia or salts thereof, comprising the steps of:

(a) lithiating a compound of the formula IIIa or salt thereof:

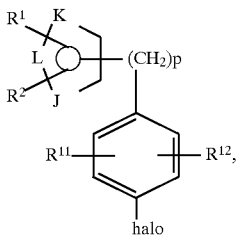

(IIIa)

preferably, a compound of the formula IIIa(1) or salt thereof, with an alkyl or aryl lithium compound in the presence of a trialkylborate, followed by hydrolysis, to form a boronic acid of the formula XIII or salt thereof:

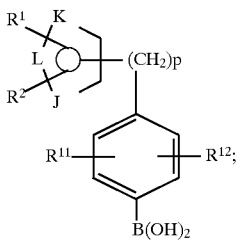

(XIII)

(b) contacting the boronic acid of the formula XIII or salt thereof with a compound of the formula VIIIa or salt thereof:

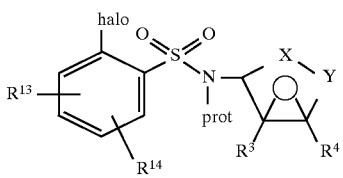

(VIIIa)

where halo is preferably bromo, iodo or chloro, most preferably bromo, in the presence of a palladium(0) catalyst and, preferably, a base, to form a nitrogen-protected compound of the formula IVa or salt thereof:

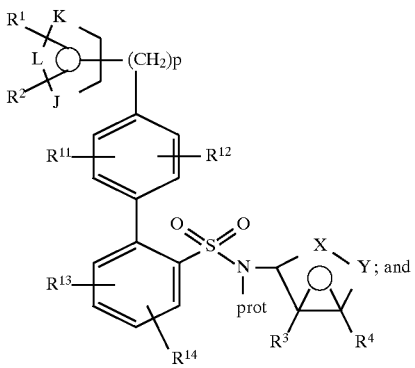

(IVa)

(c) deprotecting the nitrogen of said formula IVa compound or salt thereof to form said compound of the formula Ia or salt thereof.

With respect to this method, lithiation is conducted in the presence of a trialkylborate, followed by hydrolysis which may be conducted under conditions as described herein for the preparation of boronic acids of the formula IX and salts thereof. Coupling in the presence of a palladium(0) catalyst and, preferably, base, and deprotection of the nitrogen-protected coupled product, may be conducted under conditions as described herein for the coupling of compounds of the formulae II and III and salts thereof, and deprotection of the product thereof. Lithiation provides a compound having the following structure or a salt thereof:

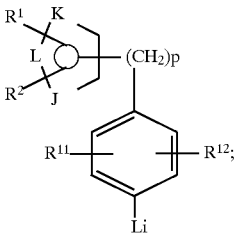

contact with a trialkylborate provides the following boronate ester or a salt thereof:

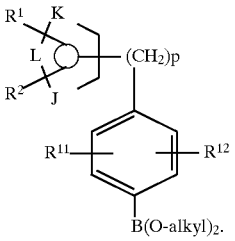

Preferred Compounds

It is preferred that the compounds employed in or prepared by the present methods contain one or more, preferably all where appropriate, of the following substituents:

X is O and N is Y;

the ring bearing K, L and J is 2-oxazole;

p is zero;

$R^1$ and $R^2$ are each independently hydrogen, alkyl, alkoxy, aryl, hydroxyalkyl, —$CO_2R^5$ or —$Z^4$—$NR^6R^7$, most preferably lower alkyl or hydrogen;

$R^3$ and $R^4$ are each independently alkyl, most preferably lower alkyl, especially methyl; and $R^{11}$, $R^{12}$, $R^{13}$ and $R^{14}$ are each independently hydrogen, hydroxy, amino, heterocyclo, alkenyl, alkoxy, carboxamide or substituted lower alkyl, most preferably, $R^{12}$ to $R^{14}$ are hydrogen and $R^{11}$ is hydrogen, hydroxy, amino, heterocyclo, alkenyl, alkoxy, carboxamide or substituted lower alkyl.

Compounds of interest include those, inter alia, wherein at least one of (i) to (iv) applies: (i) at least one of $R^{11}$, $R^{12}$, $R^{13}$ or $R^{14}$ is heterocycle, substituted heterocycle or heterocyclooxy; (ii) at least one of $Z^1$, $Z^2$ or $Z^3$ is aryl, heterocycle, substituted heterocycle or heterocyclooxy; (iii) $Z^6$ is alkyl substituted with one to three groups selected from halogen, aryl, aryloxy and alkoxy, wherein at least one substituent is other than aryl; alkyl substituted with two or three aryl groups; cycloalkyl substituted with one to three groups selected from alkyl, aryl, alkenyl and alkoxyaryl; cycloalkyl to which is fused a benzene ring; aryloxy substituted with one or two halogens; aryl substituted with methylenedioxy; aryl substituted with one to four groups selected from alkyl, dialkylamino, cyano, halogen, trihaloalkyl, alkoxy and trihaloalkoxy; or heterocycle or substituted heterocycle; or (iv) $Z^{11}$ is alkyl substituted with one, two or three halogens.

Utility of Compounds of Formula I and Salts Thereof as Endothelin Antagonists The compounds of the formula I and salts thereof are antagonists of ET-1, ET-2 and/or ET-3 and are useful in treatment of conditions associated with increased ET levels (e.g., dialysis, trauma and surgery) and of all endothelin-dependent disorders. They are thus useful as antihypertensive agents. By the administration of a composition having one (or a combination) of the compounds of this invention, the blood pressure of a hypertensive mammalian (e.g., human) host is reduced. They are also useful in pregnancy-induced hypertension and coma (preeclampsia and eclampsia), acute portal hypertension and hypertension secondary to treatment with erythropoietin.

The compounds of the present invention are also useful in the treatment of disorders related to renal, glomerular and mesangial cell function, including acute and chronic renal failure, glomerular injury, renal damage secondary to old age or related to dialysis, nephrosclerosis (especially hypertensive nephrosclerosis), nephrotoxicity (including nephrotoxicity related to imaging and contrast agents and to cyclosporine), renal ischemia, primary vesicoureteral reflux, glomerulosclerosis and the like. The compounds of this invention may also be useful in the treatment of disorders related to paracrine and endocrine function.

The compounds of the present invention are also useful in the treatment of endotoxemia or endotoxin shock as well as hemorrhagic shock.

The compounds of the present invention are also useful in hypoxic and ischemic disease and as anti-ischemic agents for the treatment of, for example, cardiac, renal and cerebral ischemia and reperfusion (such as that occurring following cardiopulmonary bypass surgery), coronary and cerebral vasospasm, and the like.

In addition, the compounds of this invention may also be useful as anti-arrhythmic agents; anti-anginal agents; anti-fibrillatory agents; anti-asthmatic agents; anti-atherosclerotic and anti-arteriosclerotic agents; additives to cardioplegic solutions for cardiopulmonary bypasses; adjuncts to thrombolytic therapy; and anti-diarrheal agents. The compounds of this invention may be useful in therapy for myocardial infarction; therapy for peripheral vascular disease (e.g., Raynaud's disease and Takayashu's disease); treatment of cardiac hypertrophy (e.g., hypertrophic cardiomyopathy); treatment of primary pulmonary hypertension (e.g., plexogenic, embolic) in adults and in the newborn and pulmonary hypertension secondary to heart failure, radiation and chemotherapeutic injury, or other trauma; treatment of central nervous system vascular disorders, such as stroke, migraine and subarachnoid hemorrhage; treatment of central nervous system behavioral disorders; treatment of gastrointestinal diseases such as ulcerative colitis, Crohn's disease, gastric mucosal damage, ulcer and ischemic bowel disease; treatment of gall bladder or bile duct-based diseases such as cholangitis; treatment of pancreatitis; regulation of cell growth; treatment of benign prostatic hypertrophy; restenosis following angioplasty or following any procedures including transplantation; therapy for congestive heart failure including inhibition of fibrosis; inhibition of left ventricular dilatation, remodeling and dysfunction; and treatment of hepatotoxicity and sudden death. The compounds of this invention may be useful in the treatment of sickle cell disease including the initiation and/or evolution of the pain crises of this disease; treatment of the deleterious consequences of ET-producing tumors such as hypertension resulting from hemangiopericytoma; treatment of early and advanced liver disease and injury including attendant complications (e.g., hepatotoxicity, fibrosis and cirrhosis); treatment of spastic diseases of the urinary tract and/or bladder; treatment of hepatorenal syndrome; treatment of immunological diseases involving vasculitis such as lupus, systemic sclerosis, mixed cryoglobulinemia; and treatment of fibrosis associated with renal dysfunction and hepatotoxicity. The compounds of this invention may be useful in therapy for metabolic and neurological disorders; cancer; insulin-dependent and non insulin-dependent diabetes mellitus; neuropathy; retinopathy; maternal respiratory distress syndrome; dysmenorrhea; epilepsy; hemorrhagic and ischemic stroke; bone remodeling; psoriasis; and chronic inflammatory diseases such as rheumatoid arthritis, osteoarthritis, sarcoidosis and eczematous dermatitis (all types of dermatitis).

The compounds of the formula I and salts thereof can also be formulated in combination with endothelin converting enzyme (ECE) inhibitors, such as phosphoramidon; thromboxane receptor antagonists; potassium channel openers; thrombin inhibitors (e.g., hirudin and the like); growth factor inhibitors such as modulators of PDGF activity; platelet activating factor (PAF) antagonists; angiotensin II (AII) receptor antagonists; renin inhibitors; angiotensin converting enzyme (ACE) inhibitors such as captopril, zofenopril, fosinopril, ceranapril, alacepril, enalapril, delapril, pentopril, quinapril, ramipril, lisinopril and salts of such compounds; neutral endopeptidase (NEP) inhibitors; dual NEP-ACE inhibitors; HMG CoA reductase inhibitors such as pravastatin and mevacor; squalene synthetase inhibitors; bile acid sequestrants such as questran; calcium channel blockers; potassium channel activators; beta-adrenergic agents; anti-arrhythmic agents; diuretics, such as chlorothiazide, hydrochlorothiazide, flumethiazide, hydroflumethiazide, bendroflumethiazide, methylchlorothiazide, trichloromethiazide, polythiazide or benzothiazide as well as ethacrynic acid, tricrynafen, chlorthalidone, furosemide, musolimine, bumetanide, triamterene, amiloride and spironolactone and salts of such compounds; and thrombolytic agents such as tissue plasminogen activator (tPA), recombinant tPA, streptokinase, urokinase, prourokinase and anisoylated plasminogen streptokinase activator complex (APSAC). If formulated as a fixed dose, such combination products employ the compounds of this invention within the dosage range described below and the other pharmaceutically active agent within its approved dosage range. The compounds of this invention may also be formulated with, or useful in conjunction with, antifungal and immunosuppressive agents such as amphotericin B, cyclosporins and the like to counteract the glomerular contraction and nephrotoxicity secondary to such compounds. The compounds of this invention may also be used in conjunction with hemodialysis.

The compounds of the invention can be administered orally or parenterally to various mammalian species known to be subject to such maladies, e.g., humans, in an effective amount within the dosage range of about 0.1 to about 100 mg/kg, preferably about 0.2 to about 50 mg/kg and more preferably about 0.5 to about 25 mg/kg (or from about 1 to about 2500 mg, preferably from about 5 to about 2000 mg) in single or 2 to 4 divided daily doses.

The active substance can be utilized in a composition such as tablet, capsule, solution or suspension containing about 5 to about 500 mg per unit dosage of a compound or mixture of compounds of formula I or in topical form for wound healing (0.01 to 5% by weight compound of formula I, 1 to 5 treatments per day). They may be compounded in a conventional manner with a physiologically acceptable vehicle or carrier, excipient, binder, preservative, stabilizer, flavor, etc., or with a topical carrier such as Plastibase (mineral oil gelled with polyethylene) as called for by accepted pharmaceutical practice.

The compounds of the invention may also be administered topically to treat peripheral vascular diseases and as such may be formulated as a cream or ointment.

The compounds of formula I can also be formulated in compositions such as sterile solutions or suspensions for parenteral administration. About 0.1 to 500 milligrams of a compound of formula I is compounded with a physiologically acceptable vehicle, carrier, excipient, binder, preservative, stabilizer, etc., in a unit dosage form as called for by accepted pharmaceutical practice. The amount of active substance in these compositions or preparations is such that a suitable dosage in the range indicated is obtained.

The present invention will now be further described by the following working examples, which illustrate preferred embodiments of the invention.

EXAMPLE 1

PREPARATION OF PINACOL ESTER II N-[(2-Methoxyethoxy)methyl]-N-(3,4-dimethyl-5-isoxazolyl-2-(4,4,5,-tetramethyl-1,3,2-dioxaborolan-2-yl)benzenesulfanamide

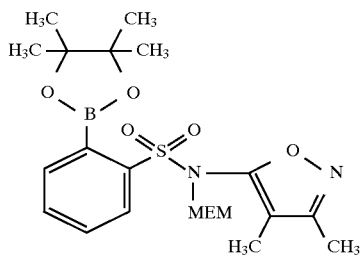

A. 2-Bromo-N-(3,4-dimethyl-5-isoxazolyl)benzenesulfonamide

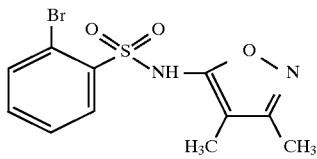

A 2 L three necked flask, equipped with an overhead mechanical stirrer, a 250 mL addition funnel and an argon line, was charged with 2-bromobenzenesulfonyl chloride (150 g, 587 mmol, commercially available) and anhydrous pyridine (150 mL). The resulting light yellow solution was cooled to −18° C. (internal temperature) by an ice/salt bath. With stirring, a solution of 5-amino-3, 4-dimethylisoxazole (69.1 g, 616 mmol, commercially available) in anydrous pyridine (195 mL) was added dropwise through the addition funnel in 1 hour. The internal reaction temperature did not exceed −6° C. during the course of the addition. After the addition, the ice/salt bath was removed and the reaction mixture was then warmed up to room temperature, stirred for 1 hour, and then stirred at 40° C. for, 21 hours.

The reaction mixture was cooled to room temperature and poured into a mixture of ice water (3 L) and celite (37.5 g). After stirring for 20 minutes, it was filtered and rinsed with water (250 mL×3). Charcoal (45 g) was added to the filtrate. The mixture was stirred at room temperature for 40 minutes and was filtered through a pad of celite. The celite pad was rinsed with water (500 mL×3). The filtrate was acidified by dropwise addition of cold HCl (6N, 750 mL) with vigorous stirring over 2 hours. Precipitation of the product occurred and the mixture was stirred for another 1 hour after the addition of HCl.

The mixture was filtered, the solid was rinsed with cold water (750 mL×4), and suction dried for 3 days. The title compound of this step was obtained as a yellowish white solid (171 g) in 88% yield (HPLC area percent =97.4%).

Thin layer chromatography (TLC): Rf=0.47
(Silica gel from Whatman; Ethyl acetate (EtOAc) :hexanes/1:1; Visualization CAM or UV)

Alternative preparation for title compound of this step

A 1 L three necked flask was charged with 2-bromobenzenesulfonyl chloride (50 g, 196 mmol) and anhydrous 1,2-dichloroethane (125 mL) under an argon atmosphere. The resulting colorless solution was cooled to 0° C. and anhydrous pyridine (40 mL, 396 mmol) was added, followed by the addition of 5-amino-3, 4-dimethylisoxazole (24.1 g, 196 mmol) as a solid. After the addition, the ice bath was removed and the reaction mixture was heated to 55° C. for 21 hours, yielding a crude reaction mixture containing the title compound of this step.

B. 2-Bromo-N-(3,4-dimethyl-5-isoxazolyl)-N-[(2-methoxyethoxy)methyl]benzenesulfonamide

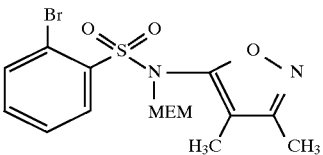

A 1 L three necked flask, equipped with a mechanical stirrer, was charged with potassium carbonate (130.5 g, 944 mmol) and anhydrous dimethylformamide (DMF, 286 mL) under an argon atmosphere. The heterogeneous mixture was stirred for 15 minutes at room temperature. The title compound of step A (125 g, 378 mmol) was added as a solid. The mixture was stirred again for 15 minutes at room temperature. Methoxyethoxymethylchloride (MEMCl, 47.5 mL, 415.8 mmol) was added dropwise through an addition funnel in 40 minutes. After the addition, the reaction mixture was stirred for 40 minutes. The reaction was monitored by HPLC.

The reaction mixture was diluted with the addition of ethyl acetate (400 mL), stirred for 5 minutes and filtered. The solid was washed with ethyl acetate (200 mL×2) and hexanes (250 mL×2). The filtrate was treated with charcoal (25 g), stirred at room temperature for 1 hour and filtered through a celite pad. The celite pad was rinsed with ethyl acetate (50 mL×3). The ethyl acetate layers were combined and washed with Na$_2$CO$_3$ (1M, 500 mL). Precipitation occurred in the aqueous layer. It was suppressed by addition of water (750 mL). The aqueous layer was separated and discarded. The organic layer was washed with water (750 mL), brine (500 mL×2), dried over Na$_2$SO$_4$, filtered and concentrated to a yellowish semi-solid (157.3 g, 99% mass balance).

The residue was dissolved in ethanol (125 mL) and set aside in a freezer (0° C.) for 20 hours. Crystallization occurred. The solid was filtered and suction dried. The title compound of this step was obtained as a yellowish white solid (75.65% yield, HPLC area percent=98.2%).

TLC: Rf=0.55 (Silica gel from Whatman;
EtOAc:hexanes/1:1; visualization: CAM or UV)

Alternative preparation for the title compound of this step

The reaction mixture obtained by the alternative method for the preparation of the title compound of Step A was cooled to room temperature and concentrated at reduced pressure on a rotary evaporator to a dark thick oil (102 g) at 40° C. The dark oil (98 g, 188 mmol) was dissolved in anhydrous dichloromethane (240 mL). Diisopropylethylamine (97 mL, 4 equivalents) was added followed by dropwise addition of methoxyethoxymethyl chloride (25.7 mL, 225.6 mmol). The reaction mixture was stirred at room temperature for 4 hours.

The reaction mixture was concentrated at reduced pressure on a rotary evaporator to a thick oil, dissolved in EtOAc (400 mL) and charcoal (10 g) was added. The charcoal mixture was stirred at room temperature for 30 minutes and was filtered through a celite pad. The celite pad was rinsed with EtOAc (100 mL×3) and hexanes (200 mL×2). The filtrate was transferred to a separatory funnel and washed with water (100 mL×2), HCl (0.5N, 100 mL×2), water (100 mL×2) and brine (100 mL×2), dried over $Na_2SO_4$, filtered and concentrated to a thick oil (64.9 g, 83% mass balance).

The thick oil was dissolved in ethanol (EtOH, 65 mL), cooled to 0° C. with an ice bath, seeded with the title product of this step and stirred at 0° C. for 6 hours. Crystallization occured. The solid was filtered and suction dried. The title compound of this step was obtained as a yellowish solid (62% overall yield, HPLC area percent=98.2%).

TLC: Rf=0.55 (silica gel from Whatman;

EtOAc:hexanes/1:1; visualization: CAM or UV)

C. 2-Borono-N-(3,4-dimethyl-5-isoxazolyl)-N-[(2-methoxyethoxy)methyl]benzenesulfonamide

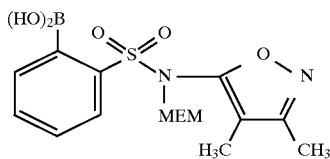

A dry 3-necked 1-liter round-bottomed flask equipped with an overhead mechanical stirrer, gas adapter, thermocouple, and septum was charged with the title compound of Step B (40.0 g; 95.4 mmol), and then thoroughly degassed and placed under an argon atmosphere. Tetrahydrofuran (THF, 185 mL) was added via syringe and the mixture was cooled to about −100° C. (internal temperature). n-Butyl lithium (n-BuLi, 42.5 mL, 101 mmol, 2.38M in hexanes) was dropwise added over a period of 16 minutes, while maintaining the internal temperature between −97° C. and −101° C. The pale yellow-orange solution was stirred at about −98° C. to −101° C. for an additional 16 minutes.

Trimethylborate (16.0 mL, 140.9 mmol) in THF (24 mL) was dropwise added over 14.5 minutes, while maintaining the internal temperature between −96° C. and −99° C. The mixture was stirred for about 44 minutes at about −93° C. to −101° C., and an additional 39 minutes at about −93° C. to −72° C. HCl (3.0N, 120 mL, 360 mmol) was added to the reaction (the solution exothermed to about −7° C.) and was stirred for 20 minutes (−7° C. to +60° C.). The two layers were separated in a separatory funnel, and the aqueous phase was washed with toluene (3×120 mL) and t-butyl methyl ether (MTBE, 3×100 mL). The combined organic layer was washed with brine (4×100 mL), dried over $Na_2SO_4$, and concentrated on a rotary evaporator to a volume of about 100 mL containing the title compound of this step (HPLC area percent=97.7%).

Alternative preparation of the title compound of this step

A 500 mL 3-neck flask equipped with a stir bar was charged with the title compound of Step B (20.0 g, 47.7 mmol) and purged with argon for 0.5 hr. Anhydrous THF (200 mL) was added via syringe and the flask was cooled to −78° C. in an acetone/dry ice bath. Phenyl lithium (PhLi, 37.1 mL, 48.2 mmol, 1.3M in cyclohexane-ether, titrated according to *J. Organomet. Chem.*, 186, 155 (1980), and determined to be 1.3M) was added via an addition funnel over the course of 25 minutes. The rate of addition of PhLi was such that the internal temperature of the reaction mixture was maintained below −75° C. The resulting solution was stirred at −78° C. for 15 minutes following which a solution of trimethylborate (10.8 mL, 95.4 mmol) in THF (5 mL) was cannulated dropwise into the reaction mixture over 15 minutes. The trimethylborate/THF solution was cooled in an ice-water bath prior to addition. The rate of addition was maintained such that the internal temperature of the reaction mixture did not go above −73° C. The reaction mixture was stirred at −78° C. for 0.5 hr, and then quenched by the dropwise addition of a solution of acetic acid (15 mL) in THF (10 mL). The acidified solution was stirred at −78° C. for 10 minutes following which the solution was warmed to 0° C. To this was added dropwise, 1N HCl (25 mL). (1N HCl was prepared by diluting 42 ml of 12N HCl into 500 mL of water. The excess acid was added in order to ensure complete quenching. The HCl solution was pre-cooled in an ice/water bath prior to addition.) The reaction mixture was then allowed to warm to room temperature and extracted with t-butyl methyl ether (TBME, 4×250 mL). The organic layers were combined and extracted with 0.5N aqueous NaOH (4×25 mL). The aqueous layers were combined and back extracted with TBME (1×100 mL). The aqueous extract was cooled to 0° C. and the pH adjusted to 2.0 (pH meter) by the dropwise addition of 6N HCl with rapid stirring. The acidified solution was extracted with TBME (4×250 mL), the organic layers pooled and dried over anhydrous $MgSO_4$. The suspension was filtered and the solution concentrated to give the boronic acid title compound of this step as a pale brown oil (17.1 g, 93%, HPLC area percent=88%).

HPLC Conditions: Column—YMC ODS-A, 6×250 mm; Monitored at 233 nm; Flow rate-1.5 mL/min; Solvent A (%): $H_2O/MeOH/H_3PO_4$ 90:10:0.2; Solvent B (%): $H_2O/MeOH/H_3PO_4$ 10:90:0.2; Gradient: 40% B to 100% B, linear gradient over 10 minutes, 100% B for 5 minutes, 40% B for 4 minutes; Retention time for the title compound of this step=8.3 minutes.

D. N-[(2-Methoxyethoxy)methyl]-N-(3,4-dimethyl-5-isoxazolyl)-2-(4,4,5,5-tetramethyl-1,3,2-dioxaborolan-2-yl)benzenesulfanamide

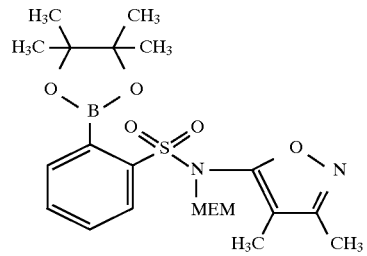

The mixture from step C was diluted with toluene (170 mL) to bring the total volume to about 270 mL, and the flask was equipped with a Dean-Stark trap and magnetic stir bar. Pinacol (11.6 g, 98.2 mmol) was added and the resulting mixture was heated to reflux for about 1.25 hr. Water was drained from the Dean-Stark trap and the solution was then used "as is" in Example 3.

(98% conversion, HPLC area percent=93.6%) Reverse phase HPLC Column: YMC-Pack ODS-A; 150×6 mm; S-5 mm, 120A and monitored @233 nm; Solvent: A=90% water, 10% methanol and 0.2% H₃PO₄; B=10% water, 90% methanol and 0.1% H3PO₄;

Flow rate: 100 mL per minute; Gradient; 40% B to 100% B in 10 minutes. Hold time: 5 minutes at 100% B. Step down to 40% B and hold for 5 minutes. Retention Time for title product of this Example-11.5 minutes.

Alternative preparation of the title compound of this Example

The boronic acid obtained in the alternative method for preparation of the title compound of Step C (17.1 g, 44.5 mmol) was dissolved in a solution of anhydrous toluene (425 mL) and pinacol (5.51 g, 46.7 mmol). The flask was placed in an oil bath and heated to 120° C. for 2 hr (note: reaction was complete in first 40 minutes) and water continuously removed by the use of a Dean-Stark trap (flask and trap covered in foil; mixture boiled rapidly in approximately 0.5 hr) and condensor. Analysis of an aliquot (worked up by repeated azeotroping with CDCl₃) by HPLC indicated complete conversion of the boronic acid starting material to the title compound of this Example. The reaction mixture was cooled to room temperature and concentrated to afford the title compound of this Example as a toluene solution, HPLC area percent=86%. A 100% yield was assumed for conversion of the boronic acid to pinacol ester. A portion of the crude solution of the title compound of this Example was used in Example 3. Retention time of title compound of this Example=12.4 minutes (using HPLC conditions described for boronic acid starting material).

EXAMPLE 2

PREPARATION OF HALOPHENYL COMPOUND III 2-(4-Iodophenyl)oxazole

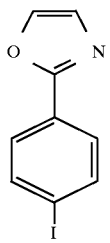

A. N-(2,2-Dimethoxyethyl)-4-iodobenzamide

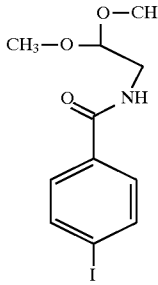

KHCO₃ (80.0 g, 0.80 mol) was added to a solution of aminoacetaldehyde dimethyl acetal (82.9 g, 86.0 mL, 0.79 mol, commercially available) in water (900 mL) and acetone (400 mL) and the resulting solution was cooled in an ice bath to 0° C. A solution of 4-iodobenzoyl chloride (200.0 g, 0.75 mol) in acetone (600 mL) was added dropwise via an addition funnel, to the aminoacetaldehyde dimethyl acetal solution over the course of 1.5 hr, with mechanical stirring. The addition funnel and the walls of the flask were washed with acetone (50 mL) and the ice bath was removed. The reaction mixture was allowed to stir at room temperature for 3 hr (reaction was completed in 1.5 hr).

The reaction mixture was concentrated by removing 1.0 L of solvent on a rotary evaporator and then extracted with EtOAc (4×350 mL). The organic layers were pooled, washed with saturated NaHCO₃ (1×250 mL) followed by H₂O (1×250 mL), dried over anhydrous MgSO₄ (50.0 g), filtered and concentrated at reduced pressure to give a white solid (during solvent evaporation, the solid was occasionally scraped off the sides of the flask). The solid was dried under house vacuum for 12 hr (246.5 g, 98%, HPLC area percent= 99.7% melting point (mp)=89°–90° C.

Elemental Analysis (%) $C_{11}H_{14}NO_3I$ Calc'd: C, 39.42; H, 4.21; N, 4.18 Found: C, 39.42; H, 4.22; N, 4.07

B. 2-(4-Iodophenyl)oxazole

Eaton's reagent was prepared by adding P₂O₅ (200 g) in approximately 50 g portions to methanesulfonic acid (2000 mL) at 95° C. under argon with vigorous mechanical stirring. The addition of P₂O₅ in portions prevented it from forming a hard mass at the bottom of the flask. A clear, very pale brown solution was obtained. Eaton et al. *J. Org. Chem.*, 38, 4071–4073 (1973).

A 3 L 3-neck round-bottom flask containing the Eaton's reagent (2000 mL) was equipped with a condenser and charged with the title compound of step A (200.0 g, 0.60 mol). The reaction mixture was placed in an oil bath and heated with stirring, under a positive pressure of argon. (It was found to be beneficial to warm the reaction mixture to the required temperature rather than set it in a pre-heated bath.) Monitoring the reaction by TLC indicated that the first step of the reaction was hydrolysis of the dimethylacetal group to the corresponding aldehyde (Rf=0.11):

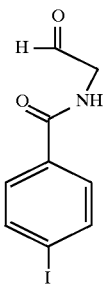

followed by cyclization. The oil bath temperature was adjusted so as to maintain the internal temperature of the reaction mixture between 130°–134° C. (The temperature of the oil bath was maintained between 138°–141° C). After 7.5 hr, analysis of an aliquot (worked up by addition to H₂O and extraction with EtOAc) by TLC indicated the complete disappearance of the starting material and the production of a single new spot.

The reaction mixture was cooled to 30° C. under argon, divided into three approximately equal portions, and each portion was poured onto a slurry of ice/water (approximately 6.0 L) with vigorous stirring using a mechanical stirrer, with external cooling. This resulted in the formation of-a brownish-gray precipitate. The resulting suspension was stirred for 2 hr and the solid was collected by suction filtration through a medium porosity sintered glass funnel, washed with ice cold water (1 L) and the filter cake broken. The solid was air dried for 5 days to give a gray powder (151.7 g, 93%). The crude material (151.7 g) was dissolved in acetonitrile (2 L) (by warming gently with a heat gun; a small amount of black flocculent solid remained undissolved in the flask) and activated charcoal (15.2 g) was added and the mixture stirred at room temperature for 1 hr. The mixture was filtered through a pad of celite (100.0 g). The celite pad was washed with acetonitrile (2×100 mL). The filtrate was concentrated under reduced pressure to approximately 1180 mL in a 5 L round bottom flask. The flask was warmed with a heat gun until the solid completely dissolved. To the resulting hot solution, boiling water (295 mL) was added in two portions, the flask was heated to near boiling and gently swirled after each addition. The solution was once again heated to near boiling, the flask was covered and allowed to stand at room temperature for 48 hr (some crystals were observed within 1.5 hr), following which it was stored at 4° C. for 4 days. The crystals which formed were collected by suction filtration and washed with an ice cold solution of acetonitrile:water (4:1, 150 mL), and air dried for 20 hr. The title compound of this Example was obtained as very pale yellow crystals which were further dried under house vacuum (107.2 g, 66%, HPLC area percent=99.7%). A second crop of the title compound was collected upon recrystallization of the yellow solid obtained upon concentration of the mother liquor (27.4 g, 17%, HPLC area percent=98.4%).

m.p.=107°–109° C.

Elemental Analysis $C_9H_6NOI$ Calcd: C, 39.88; H, 2.23; N, 5.17 Found: C, 40.00; H, 2.09; N, 5.14

EXAMPLE 3

PREPARATION OF FORMULA I COMPOUND N-(3,4-Dimethyl-5-isoxazolyl)-4'-(2- oxazolyl) [1, 1'-biphenyl]-2-sulfonamide COUPLING OF PINACOL ESTER II AND HALOPHENYL COMPOUND III

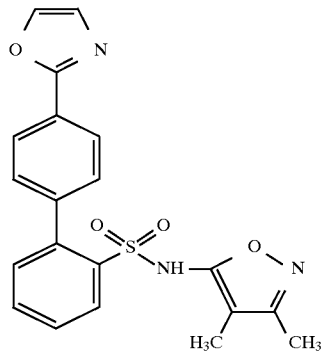

A. N-[(2-Methoxyethoxy)methyl]-N-(3,4-dimethyl-5-isoxazolyl)-4'-oxazol-2-yl-[1,1'-biphenyl]-2-sulfonamide

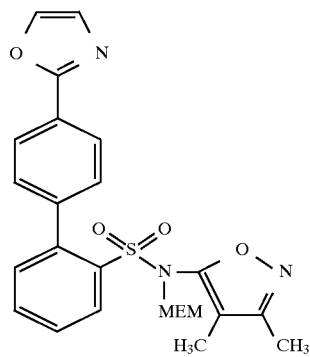

A dry 3-necked, 2-liter round-bottomed flask equipped with an overhead mechanical stirrer, gas adapter, thermocouple, reflux condenser, and septum was charged with palladium acetate (Pd(OAc)$_2$, 0.54 g, 2.38 mmol) and triphenylphosphine (Ph$_3$P, 1.7 g, 6.44 mmol), degassed and placed under an argon atmosphere. THF (85 mL) was added and the mixture was heated at 65° C. for 70 minutes. The solution gradually changed from rust orange to bright yellow in color. A degassed, toluene (270 mL) solution of the title compound of Example 2 (25.9 g, 95.6 mmol) and the crude title compound of Example 1 as prepared above (see step D of Example 1, 44.45 g, 95.4 mmol) was added via syringe followed by degassed 95% ethanol (EtOH, 285 mL), and a degassed 2.0M Na$_2$CO$_3$ solution (306 mL, 612 mmol). The resultant red colored solution was heated at about 75° C. (internal temperature) for about 1.75 hr. The heating bath was removed, and the mixture was allowed to cool to ambient temperature. The layers were separated in a separatory funnel, water (250 mL) was added and the aqueous layer was washed with CH$_2$Cl$_2$ (6×400 mL). The combined organic layers were dried over MgSO$_4$, treated with neutral charcoal (Norit, 5.0 g), filtered through celite, concentrated, and kept under dynamic, high vacuum overnight to afford the title compound of this step (62.4 g, 140%) as a red colored oil. (HPLC area percent>85%.)

Alternative preparation of the title compound of this step

Catalyst Preparation

A 2 L three necked flask equipped with overhead mechanical stirrer, reflux condenser, and argon inlet was charged with Pd(OAc)$_2$ and triphenylphosphine. The flask was purged with a slow bleed of argon for 18 hr. Anhydrous, degassed THF (67 mL) was added via syringe, the flask immersed in an oil bath preheated to 75° C., and stirred. After 20 minutes, the internal temperature reached 60° C. The mixture was stirred for 1 hr at which time it was burgundy in color, then cooled to room temperature under a slight head pressure of argon. See *J. Org. Chem.*, 1994, 59, 8151; *Organometallics*, 1992, 11, 3009.

Coupling

The title compound of Example 2 (10.0 g) was added to a portion of the toluene solution of pinacol boronate prepared in the alternative preparation of the title compound of step D of Example 1 (110 mL, 38.74 mmol of the pinacol boronate, 87% of total volume of crude boronate solution). The mixture was swirled, anhydrous ethanol (55 mL) was added, the flask sealed with a septum and swirled until a solution was obtained. The solution was degassed by bubbling argon into the solution at a moderate rate for 1 hr. The solution was then charged into the reaction vessel containing the cooled solution of catalyst via cannula under a positive pressure of argon. The flask was rinsed with anhydrous, degassed ethanol (55 mL) and transferred via cannula to the reaction vessel under a positive pressure of argon. A degassed 2M Na$_2$CO$_3$ solution (118 mL) was added via cannula, stirring was initiated, the flask immersed in a preheated oil bath at 78° C., and the internal temperature brought to 69°–70° C. HPLC and TLC analysis after 1.75 hr indicated that the reaction was complete. After 2 hr of reaction time, the mixture was cooled to 27° C., and water (100 mL) and EtOAc (100 mL) were added with stirring. The mixture was transferred to a separatory funnel, the layers separated, and the aqueous extracted with EtOAc (3×100 mL, 1×50 mL). The combined organics were washed with half-brine (1×60 mL) and dried over anhydrous MgSO$_4$ (40 g) with stirring. The solution was filtered, and the initial flask and filter funnel washed with EtOAc (2×100 mL). This process afforded a crude coupling solution with a total volume of 785 mL. HPLC analysis afforded a crude HPLC area percent of 88.9%. The solution was divided into portions for purification evaluation. For example, 5% by volume of the crude coupling solution (39 mL) was taken and concentrated on a rotary evaporator. The residue was dissolved in toluene (12 mL), C (0.9 g, 100 wt %) was added and the mixture stirred in an 88° C. oil bath for 30 min. Trithiocyanuric acid (TMT, 407 mg, 2.3 mmol, 50 mol equiv relative to assumed Pd content) was added and the mixture stirred for 30 minutes in the oil bath, cooled to 0° C. in an ice bath, filtered through celite, the celite pad rinsed with toluene (2×10 mL), and the filtrate washed with 1N NaOH (2×10 mL). The phase separation required ~3 minutes. The toluene layer was dried over MgSO$_4$, filtered and concentrated to afford the crude title compound of this step, 0.76 g, 87% mass balance. The palladium content was determined to be <1 ppm. Further experimentation indicated that 25 equivalents of TMT were adequate to reduce Pd to <10 ppm.

10% by volume of the crude coupling solution (78 mL) described above was stirred with 50 weight % C (0.9 g) to ~60° C. and allowed to cool for 30 minutes, filtered through celite, rinsed with EtOAc, and this process repeated with a fresh portion of charcoal. The solution was concentrated to afford 2.29 g (131% mass balance). The residue was azeotroped twice with anhydrous ethyl ether. The residue was dissolved in ether (11 mL), the solution cooled to 0° C., seeded with the title compound and stirred. A solid precipitated from solution. After 1 hr, hexanes (5 mL) were added dropwise, the mixture stirred at 0° C. for 2 hr, collected and washed with ice-cold 2:1 ether:hexane, affording the title compound of this step (1.07 g, 58% from the title compound of step B of Example 1) as a faint yellow powder, HPLC area percent=95.8% (in process).

HPLC Conditions

Column—YMC ODS-A, 6×250 mm

Monitored at 233 nm,

Flow Rate—1.5 mL/min.

Solvent A (%): H$_2$O/MeOH/H$_3$PO$_4$ 90:10:0.2

Solvent B (%): H$_2$O/MeOH/H$_3$PO$_4$ 10:90:0.2

Gradient: 40% B to 100% B; linear gradient over 10 min, 100% B for 5 min,

40% B for 4 min.

Retention time for the title compound of this step: 12.8 min.

Second Alternative preparation of the title compound of this step, Reverse Coupling Method A 500 L oven dried round bottom flask was charged with the title compound of Example 2 (10 g, 37.3 mmol), anhydrous THF (250 mL), toluene (50 mL) and triisopropylborate (B(OiPr)$_3$, 50 mL) under an argon atmosphere. The resulting colorless solution was cooled to −75° C. and n-butyl lithium (36 mL, 1.43M in hexanes, 51.5 mmol) was added dropwise in 1 hour. The internal temperature was kept below −73° C. during the addition. The reaction was quenched with addition of acetic acid (4 mL) in THF (25 mL) and concentrated on a rotary evaporator. Toluene (100 mL) and methanol (100 mL) were added and the solvent was removed on the rotary evaporator at 40° C. This was repeated one more time.

The resulting residue was dissolved in NaOH (100 mL, 100 mmol, 1N) and extracted with hexanes (25 mL) and TBME (25 mL) twice. The following compound was obtained:

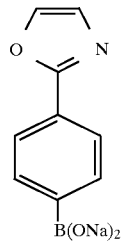

The aqueous layer was added to a mixture of NaHCO$_3$ (8.4 g, 100 mmol) in EtOH (100 mL), and a solution of the title compound of step B of Example 1 (14.4 g, 34.4 mmol) in toluene (100 mL) was added. The resulting mixture was bubbled with argon for 15 minutes.

While the above reaction was worked up, a 50 mL round bottom flask was charged with triphenylphosphine (676.8 mg, 2.58 mmol) and THF (30 mL), bubbled with argon for 15 minutes. Pd(OAc)$_2$ (193.4 mg, 0.86 mmol) was added and the mixture was heated to 65° C. for 1 hour under argon. The mixture was cooled to room temperature and was added to the above ethanol/toluene/water mixture. The resulting heterogeneous mixture was heated to 75° C. for 6 hours. HPLC indicated all starting material was consumed.

The reaction mixture was cooled to room temperature and concentrated on a rotary evaporator. Ethyl acetate (250 mL) and charcoal (10 g) were added. The mixture was stirred at room temperature for 30 minutes and filtered through a celite pad. The celite pad was rinsed with ethyl acetate (25 mL×4). The filtrate was transferred to a 500 mL separatory funnel and washed with water (100 mL×2) and brine (100 mL×2). The ethyl acetate layers were combined, mixed with trithiocyanuric acid (TMT, 4 g) and heated at 45° C. for 45 minutes. It was filtered through a celite pad. The celite pad was rinsed with ethyl acetate (25 mL×4). The organic layers were combined and washed with NaOH (200 mL×2, TMBE (300 mL) was added to minimize emulsion), water (200 mL) and brine (200 mL), dried over Na$_2$SO$_4$, filtered and concentrated to 17.5 g (98% mass balance).

The crude product was dissolved in ethanol (17.5 mL). Half of the solution (~8.8 mL) was put aside in a 0° C. freezer for 2 days. Crystallization occurred. The solid was filtered and suction dried. The product was obtained as a yellowish solid (6 g, 67% overall yield from the title compound of Example 2, HPLC area percent=99.1%.)

HPLC conditions:

Column—YMC ODS-A, 6×250 mm

Monitored at 233 nm,

Flow Rate—1.5 mL/min.

Solvent A (%): H$_2$O/MeOH/H$_3$PO$_4$ 90:10:0.2

Solvent B (%): H$_2$O/MeOH/H$_3$PO$_4$ 10:90:0.2

Gradient: 40% B to 100% B; linear gradient over 10 min, 100% B for 5 min,

40% B for 4 min.

Retention time of the title compound of this step: 12.8 min.

B. N-(3,4-Dimethyl-5-isoxazolyl)-4,-(2-oxazolyl) [1,1'-biphenyl]-2-sulfonamide

A three-necked, 3-L round-bottomed flask equipped with an overhead mechanical stirrer, a thermocouple, and a reflux condenser was charged with a bright yellow solution of the crude title compound from step A (62.45 g) in 95% ethanol (620 mL). While stirring, 6N HCl (620 mL) was added rapidly and the mixture was heated to reflux at 87° C. for 100 minutes, resulting in a pale orange solution. The reaction mixture was cooled to room temperature followed by cooling to ~0°–4° C. using an ice bath and was then basified to pH ~13 using 5N NaOH (~850 mL). The sodium hydroxide solution was added slowly over 10 minutes without allowing the temperature to rise over 30° C. The mixture was recooled to 0° C. and 250 mL of water was added and the resulting precipitate was filtered and washed with water (200 mL). The filtrate was concentrated under vacuum on a rotary evaporator at ~40° C. to remove most of the ethanol. Precipitation of the sodium salt of the title compound of this Example occurred during the concentration. The suspension was cooled to ~10° C. and filtered and washed with brine (2×150 mL). The solid was air dried for 15 minutes and transferred to a 2-L flask and dissolved in 1-L of hot water. The solution was polish filtered and washed with water (150 mL) and transferred to a 2-L separatory funnel. The aqueous layer was washed with 1:1 ethyl acetate:hexane (2×1-L) and hexane (500 mL). The yellow aqueous layer was then cooled to ~7° C. and while stirring vigorously, very slowly acidified from pH ~9.0 to 2.6 to precipitate the the title compound of this Example. After stirring for ~10 minutes the slurry was filtered and washed with excess water to remove any residual acid and air dried to afford 31.5 g (84%) of product as an off-white solid.

A 5.0 g portion of the above solid was dissolved in ethyl acetate (25 mL) and treated with trithiocyanuric acid (TMT, 0.23 g). The TMT is a chelating agent added to facilitate removal of residual palladium from the product. The mixture was gently boiled and then heated in an oil bath for 15 minutes at ~65° C. Norit charcoal (5.1 g) was added to the mixture and heating was continued for an additional 30 minutes. The mixture was then cooled in an ice bath and filtered through a bed of celite and washed with ethyl acetate (25 mL). The filtrate was transferred to a separatory funnel and washed with 1.0N HCl (1×75 mL) and water (1'75 mL). The HCl wash removed residual TMT. The organic layer was then treated with Norit charcoal (0.5 g), heated to a gentle boil and filtered through a bed of celite. The filtrate was concentrated and the residue was dissolved in absolute ethanol (20 mL), boiled and then water (10 mL) was added. The solution was seeded and allowed to cool with stirring and crystallize over 16 hours. The resultant crystals were filtered, washed with ethanol:water (1:1; 10 mL) and vacuum dried to afford 4.0 g of pure title compound of this Example (overall yield of 66% from the title compound of step A, HPLC area percent=99.02%).

m.p.=145.1° C. (high melt polymorph)

EXAMPLE 4

PREPARATION OF FORMULA I COMPOUND
N-(3,4-Dimethyl-5-isoxazolyl)-4'-(2-oxazolyl) [1,1'-biphenyl]-2-sulfonamide COUPLING OF BORONIC ACID SALT IX WITH IODOPHENYL COMPOUND III

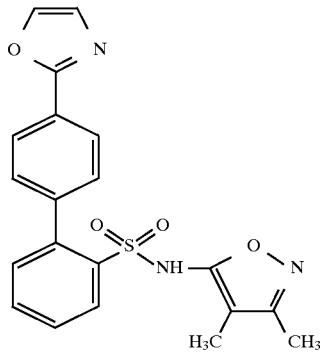

A. 2-Borono-N-(3,4-dimethyl-5-isoxazolyl)-N-[(2-methoxyethoxy)methyl]benzene-sulfonamide, disodium salt

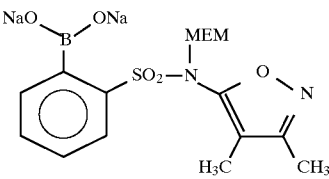

A dry 3-necked 100 mL round-bottomed flask which was equipped with: magnetic stir bar, gas adapter, thermocouple, and septum was charged with the title compound of step B of Example 1 (5.0 g; 5 11.9 mmol), and then thoroughly degassed and placed under an argon atmosphere. THF (23 mL) was added via a syringe and the mixture was cooled to –100° C. (internal temperature) and vigorously stirred. While vigorously stirring the mixture, n-BuLi (5.30 mL, 12.6 mmol) was dropwise added over a period of 19 minutes, while maintaining the internal temperature between –95° C. and –100° C. The pale yellow-orange solution was stirred for an additional 12 minutes at about –100° C. Trimethylborate (2.0 mL, 17.6 mmol) dissolved in THF (3.0 mL) was dropwise added over 12.0 minutes, while maintaining the temperature between –95° C. and –100° C. The mixture was stirred for about 50 minutes at about –95° C. to –100° C., and then stirred for an additional 40 minutes at about –78° C. to –72° C. The borate ester was hydrolyzed by the addition of 1.0N HCl (2.0 mL, 2.0 mmol) at about –72° C., the solution was warmed to ambient temperature and stirred for about 60 minutes. A solution of $Na_2CO_3$ (55 mL, 2.0M, 110 mmol) was added, and the mixture was thoroughly degassed and placed under an atmosphere of argon. This material was then used "as is" in the following steps (purity=95.9%, HPLC). YMC ODS-A column, 150 mm×6.0 mm, S-3 μm, 120 A; flow rate 1.0 mL/min. At 0.0 min. the solvent system was composed of A (40%) (A=90% MeOH/10% $H_2O$/0.1% $H_3PO_4$) and B (60%) (B=90% $H_2O$/10% MeOH/0.2% $H_3PO_4$). At 15.0 min the solvent composition was 100% A. From 15.1 min to 20.0 min the solvent composition was A (40%) and B (60%). Retention time Rt for the title compound of this step was 7.5 min. The detector was operating at 233 rim.

B. N-[(2-Methoxyethoxy)methyl]-N-(3,4-dimethyl-5-isoxazolyl)-4'-oxazol-2-yl-[1,1'-biphenyl]-2-sulfonamide

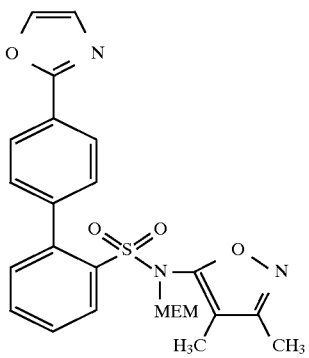

A dry 3-necked, 300 mL round-bottomed flask which was equipped with: a mechanical stirrer, gas adapter, thermocouple, reflux condenser, and septum was charged with Pd(OAc)$_2$ (0.16 g, 0.71 mmol) and Ph$_3$P (0.5 g, 1.93 mmol), degassed and placed under an argon atmosphere. THF (30 mL) was added and the mixture was heated at ~65° C. for about 70 minutes. The color gradually changed from rust-orange to yellow. A degassed solution of toluene (85 mL) and EtOH (64 mL) solution of the title compound of Example 2 (3.23 g, 11.9 mmol) was added via a syringe followed by the degassed solution of the title compound of Step A. The red colored solution was heated at ~75° C. (internal temperature) for 1.5 hr. The heating bath was removed, and the mixture was allowed to cool to ambient temperature. The layers were separated in a separatory funnel, water (50 mL) was added to the aqueous layer and the aqueous layer was extracted with EtOAc (3×200 mL). The combined organic layers were washed with brine (1×75 mL), dried with MgSO$_4$, treated with 5.0 g of Norit neutral charcoal, filtered through celite, concentrated, and kept under vacuum (about 0.1 mm Hg) overnight to afford the title compound of this step (6.17 g, 111%) as a red colored oil. (purity>80%, HPLC)

C. N-(3,4-Dimethyl-5-isoxazolyl)-4'-(2-oxazolyl) [1,1'-biphenyl]-2-sulfonamide

A dry 250 mL round-bottomed flask equipped with a reflux condenser and magnetic stir bar was charged with the crude product of step B (6.17 g, theoretical 5.56 g, 11.9 mmol), 95% EtOH (60 mL), 6.0N HCl (60 mL) and heated at reflux for 2 hr. The mixture was cooled to approximately 5° C., aqueous NaOH added to pH approximately 13 with a moderate temperature rise to less than approximately 25° C., polish filtered, and water (50 mL) was added. The solution was concentrated at 40° C. to remove most of the EtOH (~55–60 mL), whereupon a white solid formed. The mixture was cooled to 0° C. for 20 minutes, filtered and the resultant white solid was washed with brine (2×50 mL), and then dryed under vacuum (~0.1 mm Hg) for 12 hr. The white solid was dissolved in hot water (80 mL) and polish filtered. The aqueous solution was placed in a separatory funnel and washed with 1/1 EtOAc/hexanes (2×50 mL) and hexanes (75 mL). The solution was cooled to 0° C., stirred vigorously, 1.0N HCl was slowly added until pH=1.0, and then the mixture was kept at 0° C., for 15 minutes. It was filtered and washed with water (3×50 mL) to afford an off-white solid, which was suction dried for 3 hr. The white solid was then dissolved in EtOAc (65 mL), trithiocyanuric acid (0.20 g, 1.13 mmol) was added and the mixture was stirred at 65° C. for 30 minutes. Charcoal (Norit neutral, 5.0 g) was added and the mixture was stirred for an additional 30 minutes at 65° C. The mixture was cooled to 0° C., filtered through a pad of celite, washed with EtOAc (3×50 mL), and concentrated to a volume of ~60 mL. The mixture was washed with 1.0N NaOH (3×50 mL), and to the aqueous layer was added NaCl (3.0 g, 637 mmol) as well as brine (50 mL). The aqueous mixture was cooled to 0° C., filtered, and washed with brine (2×50 mL). The resultant white solid was dissolved in hot water (200 mL), cooled to 0° C., stirred vigorously, and 1.0N HCl was slowly added until pH=1.0, and the mixture was kept at 0° C. for 15 minutes. It was filtered and washed with water (3×50 mL) affording an off-white solid, which was dryed at ~45° C. under vacuum (0.1 mm Hg) for ~16 hr to afford 2.4 g (50% yield) of an off-white solid. The solid (2.25 g) was dissolved in 95% EtOH/water (9.0 mL/5.0 mL) at 70° C. Slow cooling to ambient temperature (1.5 hr) followed by cooling to 5° C. overnight afforded a white crystalline material, which was filtered and washed with cold 95% EtOH/water (3.0 mL/ 5.0 mL) and dryed under vacuum (~0.1 mm Hg) for 48 hr to afford 2.1 g of the title compound of this Example as a white solid (46.9% overall yield from the title compound of step B). TLC indicated (2/1 hexane/EtOAc, stain KMnO$_4$) that the reaction was completed after 2 hours. m.p.=143.07° C.

What is claimed is:

1. A method for the preparation of a biphenyl sulfonamide of the following formula I:

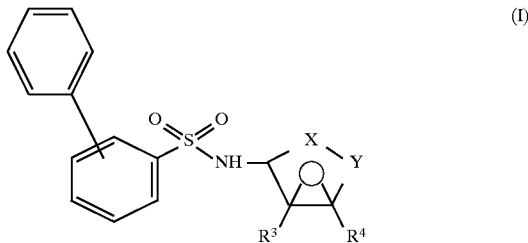

where the phenyl rings of the biphenyl group may independently be unsubstituted or substituted with one or more substituent groups, enantiomers and diastereomers, and salts thereof, wherein:

one of X and Y is N and the other is O;

R$^3$ and R$^4$ are each directly bonded to a ring carbon and are each independently
 (a) hydrogen;
 (b) alkyl, alkenyl, alkynyl, alkoxy, cycloalkyl, cycloalkylalkyl, cycloalkenyl, cycloalkenylalkyl, aryl, aryloxy, aralkyl or aralkoxy, any of which may be substituted with Z$^1$, Z$^2$ and Z$^3$;
 (c) halo;
 (d) hydroxyl;
 (e) cyano;
 (f) nitro;
 (g) —C(O)H or —C(O)R$^5$;
 (h) —CO$_2$H or —CO$_2$R$^5$;
 (i) —Z$^4$—NR$^6$R$^7$;
 (j) —Z$^4$—N(R$^{10}$)—Z$^5$—NR$^8$R$^9$; or
 (k) R$^3$ and R$^4$ together may also be alkylene or alkenylene, either of which may be substituted with Z$^1$, Z$^2$ and Z$^3$, completing a 4- to 8-membered saturated, unsaturated or aromatic ring together with the carbon atoms to which they are attached;

R$^5$ is alkyl, alkenyl, alkynyl, cycloalkyl, cycloalkylalkyl, cycloalkenyl, cycloalkenylalkyl, aryl or aralkyl, any of which may be substituted with Z$^1$, Z$^2$ and Z$^3$;

R$^6$, R$^7$, R$^8$, R$^9$ and R$^{10}$ are each independently
 (a) hydrogen; or
 (b) alkyl, cycloalkyl, cycloalkylalkyl, cycloalkenylalkyl, aryl or aralkyl, any of which may be substituted with Z$^1$, Z$^2$ and Z$^3$; or R[6] and R[7] together may be alkylene or alkenylene, either of which may be substituted with $Z^1$, $Z^2$ and $Z^3$, completing a 3- to 8-membered saturated or unsaturated ring together with the nitrogen atom to which they are attached; or any two of $R^8$, $R^9$ and $R^{10}$ together are alkylene or alkenylene, either of which may be substituted with $Z^1$, $Z^2$ and $Z^3$, completing a 3- to 8-membered saturated or unsaturated ring together with the atoms to which they are attached;

$Z^1$, $Z^2$ and $Z^3$ are each independently
(a) hydrogen;
(b) halo;
(c) hydroxy;
(d) alkyl;
(e) alkenyl;
(f) aryl;
(g) aralkyl;
(h) alkoxy;
(i) aryloxy;
(j) aralkoxy;
(k) heterocycle, substituted heterocycle or heterocyclooxy;
(l) —SH, —S(O)$_n$Z$^6$, —S(O)$_m$—OH, —S(O)$_m$—OZ$^6$, —O—S(O)$_m$—Z$^6$, —O—S(O)$_m$OH or —O—S(O)$_m$—OZ$^6$;
(m) oxo;
(n) nitro;
(o) cyano;
(p) —C(O)H or —C(O)Z$^6$;
(q) —CO$_2$H or —CO$_2$Z$^6$;
(r) —Z$^4$—NZ$^7$Z$^8$;
(s) —Z$^4$N(Z$^{11}$)—Z$^5$—H;
(t) —Z$^4$—N(Z$^{11}$)—Z$^5$—Z$^6$; or
(u) —Z$^4$—N(Z$^{11}$)—Z$^5$—NZ$^7$Z$^8$;

$Z^4$ and $Z^5$ are each independently
(a) a single bond;
(b) —Z$^9$—S(O)$_n$—Z$^{10}$—;
(c) —Z$^9$—C(O)—Z$^{10}$—;
(d) —Z$^9$—C(S)—Z$^{10}$—;
(e) —Z$^9$—O—Z$^{10}$—;
(f) —Z$^9$—S—Z$^{10}$—;
(g) —Z$^9$—O—C(O)—Z$^{10}$—; or
(h) —Z$^9$—C(O)—O—Z$^{10}$—;

$Z^6$ is alkyl; alkyl substituted with one to three groups selected from halogen, aryl, aryloxy and alkoxy; alkenyl; alkynyl; cycloalkyl; cycloalkyl substituted with one to three groups selected from alkyl, aryl, alkenyl and alkoxyaryl; cycloalkyl to which is fused a benzene ring; aryloxy substituted with one or two halogens; cycloalkylalkyl; cycloalkenyl; cycloalkenylalkyl; aryl; aryl substituted with methylenedioxy or one to four groups selected from alkyl, dialkylamino, cyano, halogen, trihaloalkyl, alkoxy and trihaloalkoxy; or heterocycle or substituted heterocycle;

$Z^7$ and $Z^8$ are each independently hydrogen, alkyl, cycloalkyl, cycloalkylalkyl, cycloalkenylalkyl, aryl or aralkyl, or $Z^7$ and $Z^8$ together are alkylene or alkenylene, completing a 3- to 8-membered saturated or unsaturated ring together with the nitrogen atom to which they are attached;

$Z^9$ and $Z^{10}$ are each independently a single bond, alkylene, alkenylene or alkynylene;

$Z^{11}$ is
(a) hydrogen; or
(b) alkyl, alkyl substituted with one, two or three halogens, cycloalkyl, cycloalkylalkyl, cycloalkenylalkyl, aryl or aralkyl;

or any two of $Z^7$, $Z^8$ and $Z^{11}$ together are alkylene or alkenylene, completing a 3- to 8-membered saturated or unsaturated ring together with the atoms to which they are attached;

each m is independently 1 or 2; and
each n is independently 0, 1 or 2; comprising the steps of:
(a) contacting a pinacol ester of the formula II or salt thereof:

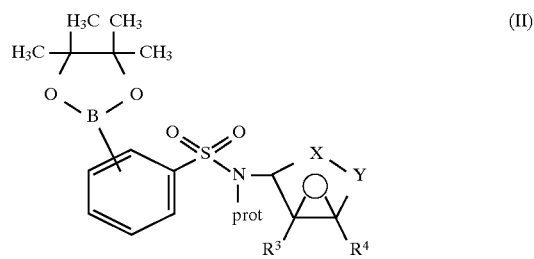

where the phenyl ring of said formula II may be further substituted, and where "prot" denotes a nitrogen-protecting group, with a halophenyl compound of the formula III or salt thereof:

where the phenyl ring of said formula III may be further substituted, in the presence of a palladium(0) catalyst and, optionally, a base, to form a nitrogen-protected compound of the formula IV or salt thereof:

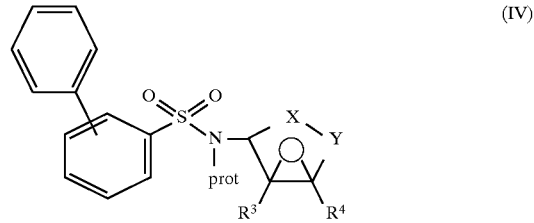

where the phenyl rings of the biphenyl group may independently be unsubstituted or substituted with one or more substituent groups; and (b) deprotecting the nitrogen of said compound of the formula IV or salt thereof to form said compound of the formula I or salt thereof.

2. The method of claim 1, for the preparation of a compound of the following formula Ia:

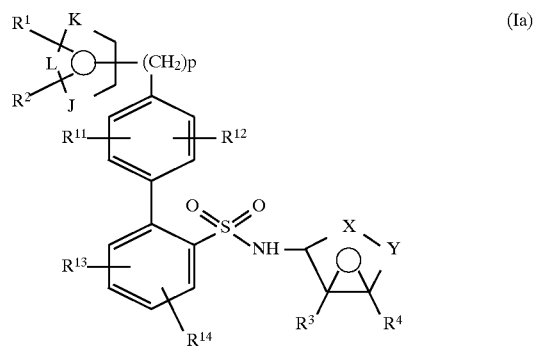

and enantiomers and diastereomers, and salts thereof, wherein:

$R^1$ and $R^2$ are each directly bonded to a ring carbon and are each independently selected from those groups (a) through (j) recited above for $R^3$ and $R^4$;

$R^{11}$, $R^{12}$, $R^{13}$ and $R^{14}$ are each independently (a) hydrogen;

(b) alkyl, alkenyl, alkynyl, alkoxy, cycloalkyl, cycloalkylalkyl, cycloalkenyl, cycloalkenylalkyl, aryl, aryloxy, aralkyl or aralkoxy, any of which may be substituted with $Z^1$, $Z^2$ and $Z^3$, (c) heterocycle, substituted heterocycle or heterocyclooxy;

(d) halo;

(e) hydroxyl;

(f) cyano;

(g) nitro;

(h) —C(O)H or —C(O)$R^5$;

(i) —CO$_2$H or —C$_2$R$^5$;

(j) —SH, —S(O)$_n$R$^5$, —S(O)$_m$—OH, —S(O)$_m$—OR$^5$, —O—S(O)m-OR$^5$, —O—S(O)$_m$OH or —O—S(O)$_m$—OR$^5$;

(k) —Z$^4$—NR$^6$R$^7$; or (l) —Z$^4$—N(R$^{10}$)—Z$^5$—NR$^8$R$^9$;

J is O, S, N or NR$^{15}$;

K and L are N or C, provided that at least one of K or L is C;

$R^{15}$ is hydrogen, alkyl, hydroxyethoxy methyl or methoxyethoxy methyl; and is 0 or an integer from 1 to 2; comprising the steps of:

(a) contacting a pinacol ester of the formula IIa or salt thereof:

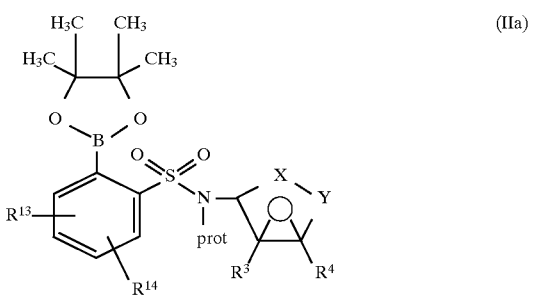

with a halophenyl compound of the formula IIIa or salt thereof:

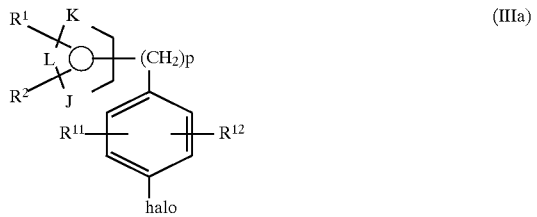

in the presence of a palladium(0) catalyst and, optionally, a base, to form a nitrogen-protected compound of the formula IVa or salt thereof:

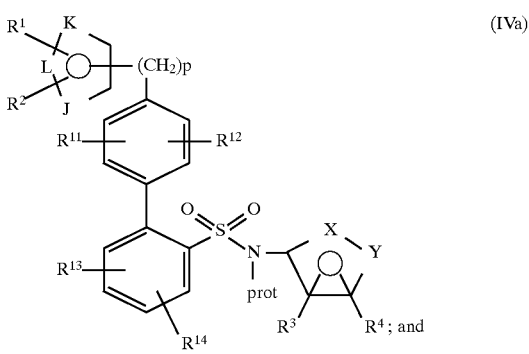

(b) deprotecting the nitrogen of said formula IVa compound or salt thereof to form said compound of the formula Ia or salt thereof.

3. The method of claim 2, wherein said palladium(0) catalyst is a palladium (II) salt which is contacted with triphenylphosphine.

4. The method of claim 3, wherein said palladium (II) salt is palladium acetate.

5. The method of claim 2, wherein said base is aqueous potassium carbonate or sodium carbonate.

6. The method of claim 2, wherein "prot" is methoxyethoxymethyl or 2-ethoxyethyl.

7. The method of claim 2, wherein the halo group in said compound of the formula IIIa or salt thereof is bromo, chloro, or iodo.

8. The method of claim 2, wherein said compound of the formula Ia or salt thereof is crystallized from solution subsequent to step (b).

9. The method of claim 2, wherein residual palladium is removed subsequent to step (a) by use of a chelating agent.

10. The method of claim 2, wherein said compound of the formula IIa or salt thereof is N-[(2-methoxyethoxy)methyl]-N-(3,4-dimethyl-5-isoxazolyl)-2-(4,4,5,5-tetramethyl-1,3,2-dioxaborolan-2-yl)benzenesulfanamide, said compound of the formula IIIa or salt thereof is 2-(4-iodophenyl)oxazole, and said compound of the formula Ia or salt thereof is N-(3,4-dimethyl-5-isoxazolyl)-4'-(2-oxazolyl) [1,1'-biphenyl]-2-sulfonamide.

* * * * *